(12) United States Patent
Corkum et al.

(10) Patent No.: US 10,596,700 B2
(45) Date of Patent: Mar. 24, 2020

(54) SYSTEM AND CALIBRATION, REGISTRATION, AND TRAINING METHODS

(71) Applicant: Carbon Robotics, Inc., San Francisco, CA (US)

(72) Inventors: Daniel Corkum, San Francisco, CA (US); Rosanna Myers, San Francisco, CA (US)

(73) Assignee: Carbon Robotics, Inc., San Francisco, CA (US)

( * ) Notice: Subject to any disclaimer, the term of this patent is extended or adjusted under 35 U.S.C. 154(b) by 208 days.

(21) Appl. No.: 15/707,648

(22) Filed: Sep. 18, 2017

(65) Prior Publication Data

US 2018/0126553 A1 May 10, 2018

Related U.S. Application Data

(60) Provisional application No. 62/395,990, filed on Sep. 16, 2016.

(51) Int. Cl.
*B25J 9/16* (2006.01)
*B25J 9/00* (2006.01)
(Continued)

(52) U.S. Cl.
CPC ........... *B25J 9/1664* (2013.01); *B25J 9/0081* (2013.01); *B25J 9/1692* (2013.01); *B25J 9/1697* (2013.01); *G05B 19/423* (2013.01); *G16H 40/63* (2018.01); *G16Z 99/00* (2019.02); *G05B 2219/39024* (2013.01); *Y10S 901/04* (2013.01);
(Continued)

(58) Field of Classification Search
CPC ...... B25J 9/1664; B25J 9/1697; B25J 9/1692; B25J 9/0081; G16Z 99/00; G16H 40/63; G05B 19/423; G05B 2219/39024; Y10S 901/47; Y10S 901/28; Y10S 901/15; Y10S 901/04
See application file for complete search history.

(56) References Cited

U.S. PATENT DOCUMENTS

| | | | | |
|---|---|---|---|---|
| 5,617,335 A | * | 4/1997 | Hashima | B25J 9/1697 340/815.57 |
| 6,236,896 B1 | * | 5/2001 | Watanabe | B25J 9/1692 414/730 |

(Continued)

*Primary Examiner* — Jason Holloway
(74) *Attorney, Agent, or Firm* — Run8 Patent Group, LLC; Peter Miller

(57) ABSTRACT

A method for manipulating a multi-link robotic arm includes: at a first time, recording a first optical image through an optical sensor arranged proximal a distal end of the robotic arm proximal an end effector; detecting a global reference feature in a first position in the first optical image; virtually locating a global reference frame based on the first position of the global reference feature in the first optical image; calculating a first pose of the end effector within the global reference frame at approximately the first time based on the first position of the global reference feature in the first optical image; and driving a set of actuators within the robotic arm to move the end effector from the first pose toward an object keypoint, the object keypoint defined within the global reference frame and representing an estimated location of a target object within range of the end effector.

20 Claims, 6 Drawing Sheets

(51) Int. Cl.
*G16H 40/63* (2018.01)
*G16Z 99/00* (2019.01)
*G05B 19/423* (2006.01)

(52) U.S. Cl.
CPC ............ *Y10S 901/15* (2013.01); *Y10S 901/28* (2013.01); *Y10S 901/47* (2013.01)

(56) References Cited

U.S. PATENT DOCUMENTS

| | | | |
|---|---|---|---|
| 7,957,583 B2 * | 6/2011 | Boca | B25J 9/1697 |
| | | | 345/419 |
| 9,919,427 B1 * | 3/2018 | Guilbert | B25J 9/1664 |
| 2004/0257021 A1 | 12/2004 | Chang et al. | |
| 2012/0199632 A1 | 8/2012 | Spivey et al. | |
| 2013/0158947 A1 * | 6/2013 | Suzuki | G01B 11/00 |
| | | | 702/155 |
| 2013/0345875 A1 | 12/2013 | Brooks et al. | |
| 2014/0277737 A1 * | 9/2014 | Sekiyama | B25J 9/1697 |
| | | | 700/259 |
| 2014/0356049 A1 | 12/2014 | Lin et al. | |
| 2015/0217444 A1 | 8/2015 | Asada et al. | |
| 2015/0246443 A1 | 9/2015 | Linnell | |
| 2016/0243704 A1 * | 8/2016 | Vakanski | B25J 9/1664 |

\* cited by examiner

SYSTEM AND CALIBRATION, REGISTRATION, AND TRAINING METHODS

CROSS-REFERENCE TO RELATED APPLICATIONS

This Application claims the benefit of U.S. Provisional Application No. 62/395,990, filed on 16 Sep. 2016, which is incorporated in its entirety by this reference.

TECHNICAL FIELD

This invention relates generally to the field of robotic arms and more specifically to a new and useful system and calibration, registration, and training methods in the field of robotic arms.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System and Method

Figure 1:
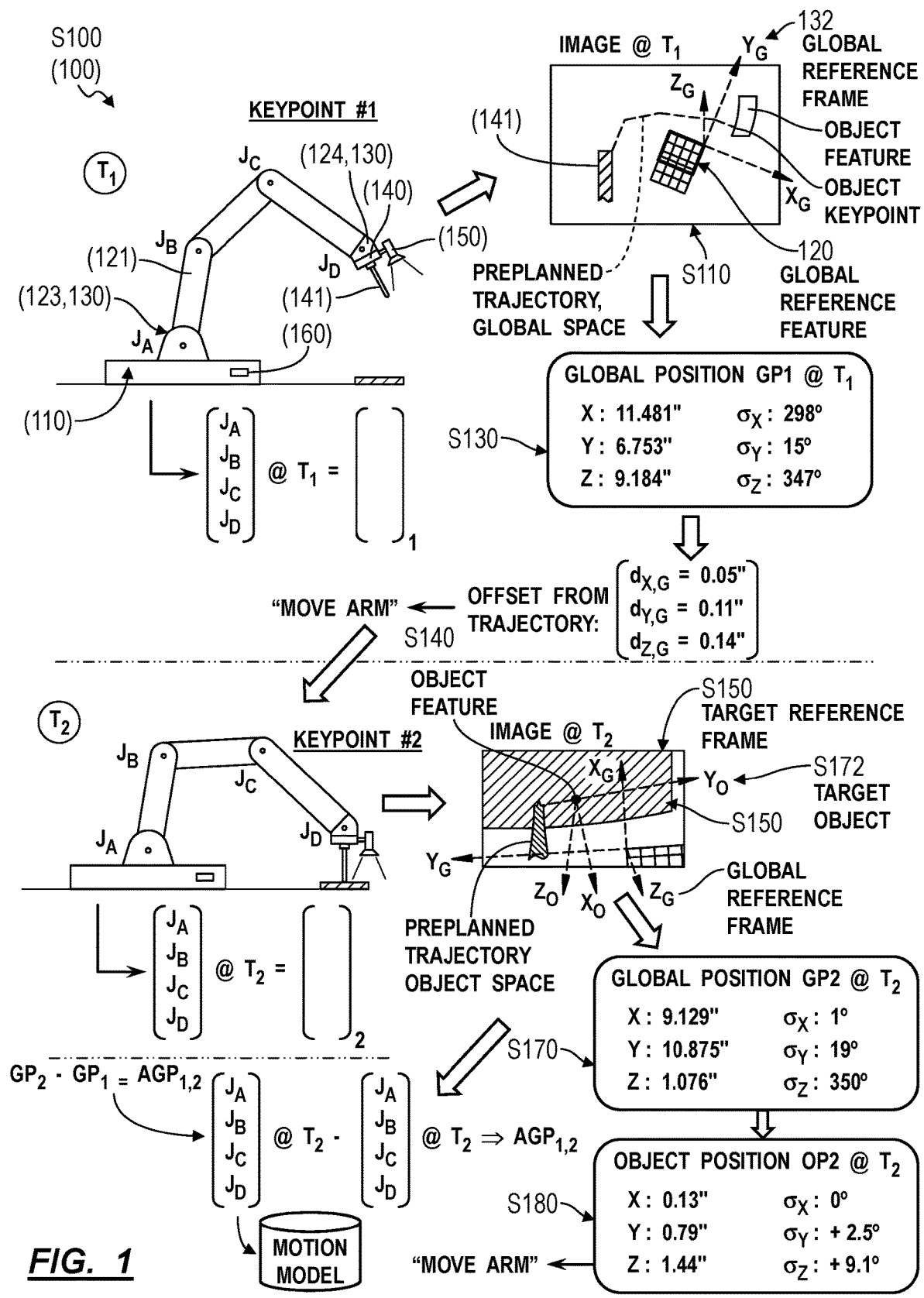
FIG. 1 is a flowchart representation of a system and a first method.

As shown in FIG. 1, a system 100 includes: a base 110, an robotic arm 120, an end effector 140, a camera 150, and a controller 160. The arm includes: a first beam 121; a first joint 123 interposed between a first beam 121 and a base 110 and comprising a first position sensor; a second beam 122; and a second joint 124 interposed between a second beam 122 and a first beam 121 and comprising a second position sensor. The end effector 140 is transiently coupled to the second beam 122 opposite the second joint 124 and defines an interface surface 141 configured to engage a target object in the vicinity of the base 110. The camera 150 is coupled to the second beam 122, defines a field of view extending toward the end effector 140, and is configured to output digital photographic images. The controller 160 is configured: to detect a like feature in a first image and a second image output by the camera 150; to determine a change in the position of the camera 150 in real space from a first pose of the end effector 140 to a second pose of the end effector 140 based on a change in the position and orientation of the feature from the first image and the second image; and to calibrate the second position sensor by mapping a difference between a first output of the second position sensor at the first position and a second output of the second position sensor at the second position to the calculated change in the position of the camera 150.

Figure 3:
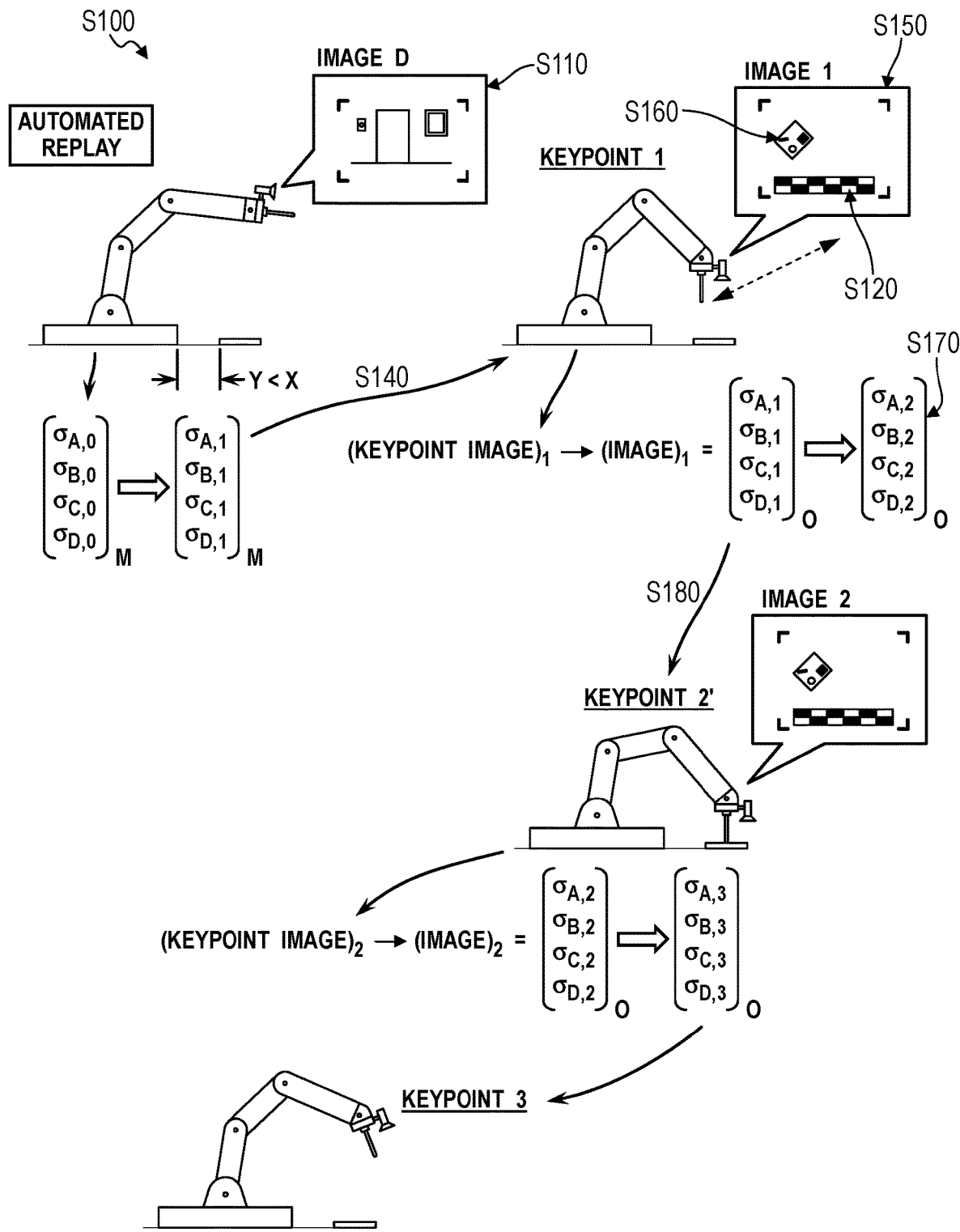
FIG. 3 is a flowchart representation of one variation of the first method.

As shown in FIG. 3, one variation of the system 100 shown includes: a base no; a first beam 121; a first joint 123 interposed between the first beam 121 and the base no; a second beam 122; a second joint 124 interposed between the second beam 122 and the first beam 121; an end effector 140 transiently coupled to the second beam 122 opposite the second joint 124 and defining an interface surface 141 configured to engage a target object in the vicinity of the base 110; and an optical sensor coupled to the second beam 122, defining a field of view extending toward the end effector 140, and configured to output optical images of the field of view. In this variation, the controller 160 is configured to: actuate the first joint 123 and the second joint 124 to move the end effector 140 from an initial pose to a first pose according to a preplanned trajectory; identify the target object in a first optical image recorded by the optical sensor when the robotic arm 120 occupies the first pose at a first time; align the preplanned trajectory to the target object based on a first position of the target object detected in the first optical image; actuate the first joint 123 and the second joint 124 to move the end effector 140 from the first pose to a second pose along the preplanned trajectory aligned to the target object; identify the target object in a second optical image recorded by the optical sensor when the robotic arm 120 occupies the second pose at a second time succeeding the first time; realign the preplanned trajectory to the target object based on a second position of the target object detected in the second optical image; and actuate the first joint 123 and the second joint 124 to move the end effector 140 from the second pose to a third pose along the preplanned trajectory aligned to the target object.

Figure 4:
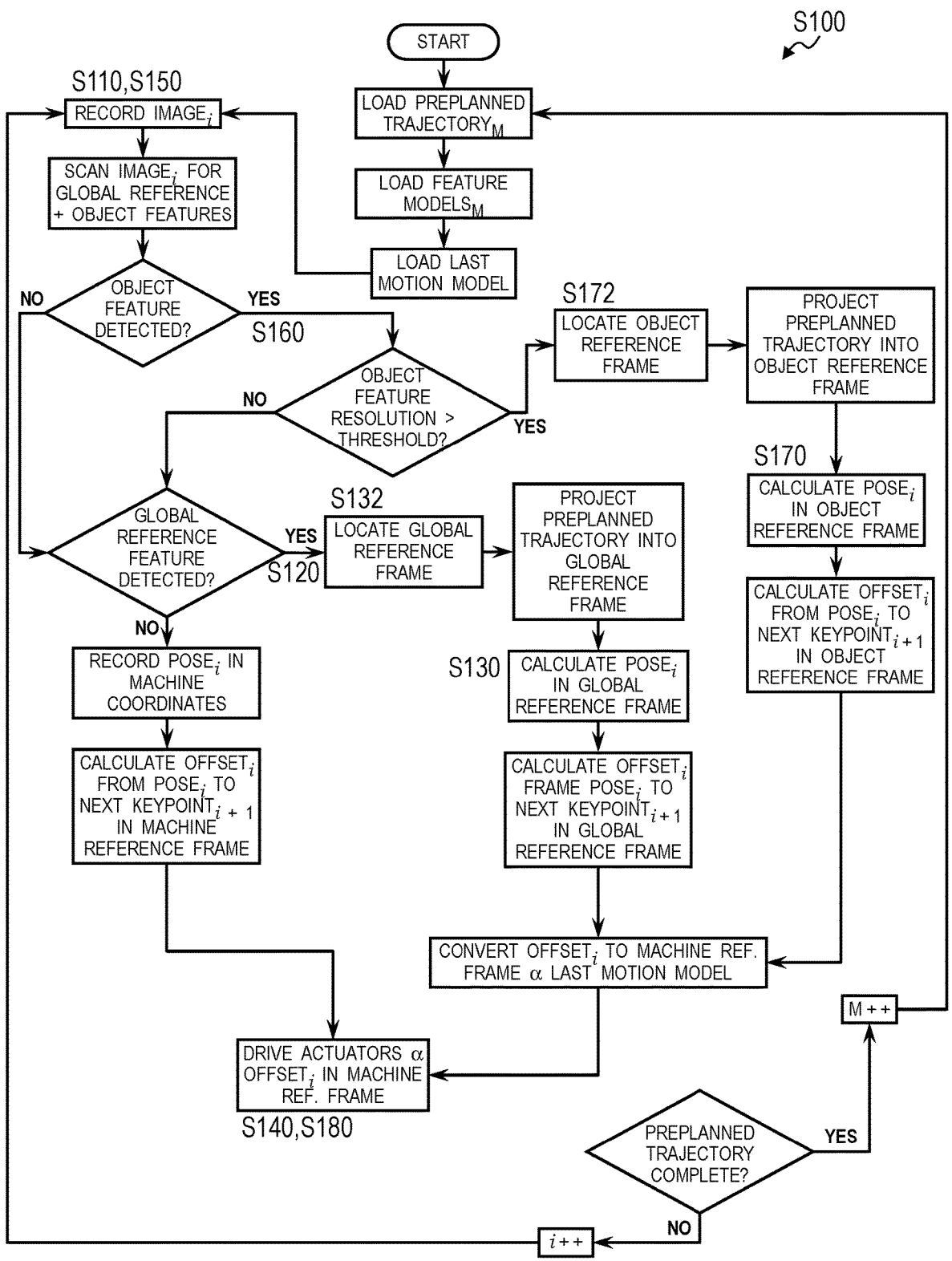
FIG. 4 is a flowchart representation of one variation of the first method.

As shown in FIGS. 1 and 4, the system 100 can therefore execute a first method S100 for manipulating a multi-link robotic arm 120, including: at a first time, recording a first optical image through an optical sensor 150 arranged proximal a distal end of the robotic arm 120 proximal an end effector 140 in Block S110; detecting a global reference feature in a first position in the first optical image in Block S120; in response to detecting the global reference feature in the first optical image, virtually locating a preplanned trajectory relative to the first position of the global reference feature in the first optical image in Block S130, the preplanned trajectory defining an object keypoint representing an estimated location of a target object within range of the end effector 140; driving a set of actuators 130 within the robotic arm 120 to move the end effector 140 along the preplanned trajectory, virtually located relative to the global reference feature, toward the object keypoint in Block S140; at a second time succeeding the first time, recording a second optical image through the optical sensor 150 in Block S150; detecting an object feature in a second position in the second optical image in Block S160, the object feature representing the target object; in response to detecting the object feature in the second optical image, virtually aligning the object keypoint of the preplanned trajectory to the object feature based on the second position of the object feature in the second optical image in Block S170; and driving the set of actuators 130 to move the end effector 140 along the preplanned trajectory, virtually aligned to the object feature, toward the target object in Block S180.

In one variation shown in FIGS. 1 and 4, the system 100 similarly executes the first method S100 by: at a first time, recording a first optical image through an optical sensor 150 arranged proximal a distal end of the robotic arm 120 proximal an end effector 140 in Block S110; detecting a global reference feature in a first position in the first optical image in Block S120; virtually locating a global reference frame based on the first position of the global reference feature in the first optical image in Block S132; calculating a first pose of the end effector 140 within the global reference frame at approximately the first time based on the first position of the global reference feature in the first optical image in Block S130; driving a set of actuators 130 within the robotic arm 120 to move the end effector 140 from the first pose toward an object keypoint, the object keypoint defined within the global reference frame and representing an estimated location of a target object within range of the end effector 140 in Block S140; at a second time succeeding the first time, recording a second optical image through the optical sensor 150 in Block S150; detecting an object feature in a second position in the second optical image, the object feature representing the target object in Block S150; calculating a second pose of the end effector 140 relative to the target object at approximately the first time based on the second position of the object feature in the second optical image in Block S110; and driving the set of actuators 130 to move the end effector 140 from the second pose toward the target object in Block S180.

2. Applications

Generally, the system 100 defines a robotic arm including multiple powered axes, a camera 150 or other optical sensor mounted to the end of the arm, an end effector 140, and a controller 160 that executes Blocks of the first method S100 to locate global- and object-based reference frames in real space, to track the pose (e.g., position and orientation in six degrees of freedom) of the end effector 140 within a reference frame or along a preplanned trajectory defined within a reference frame, and to calibrate axes of the robotic arm based on optical data collected by the camera 150 during operation of the system 100. In particular, the system 100 includes: a camera 150 mounted to the arm, arranged at a known offset from an end effector 140 (transiently) mounted to the end of the arm, and configured to intermittently record and output images, such as discrete images when triggered or in the form of a video feed (e.g., at a rate of twenty-four frames per second); and a controller 160 that calibrates various position sensors within the robotic arm and/or registers motion of the end effector 140 within real space—such as relative to a global reference feature defining a global reference frame or relative to an object feature representing a target object—based on features detected across images recorded by the camera 150 while the arm is in operation.

2.1 Applications: Object Reference Frame

As shown in FIGS. 1 and 4, the controller 160 can implement computer vision techniques described below to transform digital photographic images recorded by a camera 150 mounted to the arm (e.g., rather than to the base or mounted externally from the arm) to automatically calibrate electromechanical joints of the arm and to locate objects and surfaces near the robot in preparation to interface with objects and surfaces, thereby enabling lower precision location and geometry of such objects by external systems. The controller 160 can therefore handle optical data collected by the camera 150 as true and modify or calibrate data read from other sensors in the system 100 based on these optical data received from the camera 150.

In one implementation, the controller 160 executes Block of the first method S100 to register motion of the arm to a specific target object that system has been programmed or otherwise configured to manipulate. For example, the controller 160 can identify the target object—such as by a singular object feature or by a constellation of object features representing the target object—in a field of view of the camera 150 (i.e., in an image recorded by the camera iso) as the actuators move the end effector 140 through a preplanned trajectory. The controller 160 can: regularly realign the preplanned trajectory to the target object detected in the field of view of the camera 150, such as by virtually relocating a terminus (e.g., a final keypoint, an object keypoint) of the preplanned trajectory to coincide with the target object detected in the field of the view of the camera iso; and then drive actuators in the arm to move the end effector 140 along this preplanned trajectory that is defined in real space relative to the target object rather than based on a static virtual coordinate system (arbitrarily) assigned to the real space. In particular, by registering motion of joints of the arm to a target object that the system 100 is programmed or configured to engage (e.g., grasp, move)—rather than registering motion of the arm to a virtual coordinate system, to a secondary reference feature near the system 100, or to a joint space—the system 100 can accurately and repeatably engage the target object despite the absolute position and orientation of the target object relative to the base or how accurately the target object is located (e.g., by a fixture, dispenser, or other carrier) near the system 100.

For example, the controller 160 can: locate an object reference frame—including an object coordinate system—relative to a target object identified in an image recorded from the camera 150; orient the object reference frame in real space relative to the end effector 140 based on the position and orientation of the target object identified in the image and based on a known offset between the camera 150 and the end effector 140; project the preplanned trajectory into the object reference frame; implement closed-loop controls to move the end effector 140 along the preplanned trajectory toward the terminus of the preplanned trajectory at which the end effector 140 may accurately engage the target object; refine the location and orientation of the object reference coordinate system as the arm moves the end effector 140 and the camera 150 closer to the target object (which may yield a higher-resolution image of the target object); and repeat this process regularly—such as at a rate of 2 Hz, 20 Hz, or for every 10-millimeter interval traversed by the end effector 140—until the end effector 140 engages the target object. By thus realigning the preplanned trajectory to the target object (e.g., to an object feature or constellation of object features) detected in the field of view of the camera 150 as the end effector 140 approaches the target object, the system 100 can achieve increased locational accuracy of the end effector 140 relative to the target object as the end effector 140 nears the target object while also accommodating wide variances in the location and orientation of the target object from its expected location and orientation and/or accommodating wide variances in the location and orientation of one unit of the target object to a next unit of the target object.

Similarly, by calculating a pose of the camera 150 relative to an object feature—representing the target object—based on the position and orientation of the object feature in the field of view of the camera 150 and then applying a transform based on a known offset between the camera 150 and the end effector 140 (e.g., an interface surface on the end effector 140 configured to engage a target surface on the target object) to calculate a pose of the end effector 140 relative to the object feature, the controller 160 can register motion of the end effector 140 (or, more specifically, the interface surface on the end effector 140) directly to the target object that the system 100 has been configured to engage rather than register motion of the end effector 140 indirectly through joints to a static machine reference frame (e.g., defined relative to the base) that contains little or no information regarding the real location and orientation of the target object.

2.2 Global Reference Frame

As shown in FIGS. 1 and 4, the system 100 can implement similar methods and techniques: to track the pose of the end effector 140 within a global reference frame defined by a global reference feature detected in images recorded by the camera 150; and/or to register motion of the end effector 140 to the global reference feature detected in these images according to Blocks of the first method S100. For example, when a global reference feature is detected in an image but an object feature is either not detected in the image or is of a size insufficient to reliably locate an object reference frame, the system 100 can: virtually locate a global reference frame in real space based on the position, size, and skew of the global reference feature detected in an image; locate a preplanned trajectory within the global reference frame; calculate a pose of the end effector 140 within the global reference frame; and calculate an offset between the pose of the end effector 140 and a target position (e.g., a keypoint) along the preplanned trajectory within the global reference frame. In this example, the controller 160 can then drive the actuators to reduce this offset and to move the end effector 140 along the trajectory to a next target position. The controller 160 can regularly repeat this process—such as at a rate of 20 Hz, 2 Hz, or per ten millimeters traversed by the end effector 140, etc.—to relocate the global reference frame, calculate a new pose of the end effector 140 within the global reference frame, calculate an offset between the new pose and a target position along the preplanned trajectory, and to drive the end effector 140 back onto the preplanned trajectory and to a next target position on the preplanned trajectory.

The controller 160 can thus implement closed-loop controls to move the end effector 140 along a preplanned trajectory defined within a global reference frame registered to a known static feature in real space near the system 100, such as a checkerboard or other visually encoded surface on or near the base of the system 100. By calculating the pose of the end effector 140 within this global reference frame—rather than relative to the base via angular position sensors that inherently exhibit a positional error stack—and driving actuators in the arm according to the pose of the end effector 140 within the global reference frame, the controller 160 can achieve a relatively high degree of positional accuracy of the end effector 140 relative to the global reference feature.

2.3 Applications: Calibration

In one implementation shown in FIG. 1, the controller 160 executes Blocks of the first method S100 to: calculate changes in the pose of the end effector 140 in real space over a period of time based on changes in the position and orientation of an optical feature or fiducial in the field of view of the camera 150 during this period of time; record outputs of angular position sensors (e.g., encoders) in joints of the arm over this period of time; and calibrate outputs of the angular positions to outputs of the actuators based on changes in the pose of the end effector 140 calculated from optical data collected during this period of time. In particular, the angular position sensors in the joints of the arm may be distant from the end effector 140 at the distal end of the arm and may therefore yield a relatively low precision (or relatively large error) for global calculations of the absolute pose of the end effector 140 in a machine reference frame (e.g., relative to the base). For example, for a two-link arm: extending from a base; terminating at an end effector 140; with one-meter long links; with actuatable joints between each of the base, first link, second link, and end effector 140; and with 1000-point encoders in each joint, the accuracy of the absolute pose of the end effector 140 calculated from outputs of these angular position sensors may be one centimeter. However, by regularly recalibrating the encoders in the joints of the arm to changes of the pose of the end effector 140 calculated from positions (or changes in positions) of features in the field of view of the camera 150, the controller 160 can achieve greater accuracy in encoder-based pose calculations near a local image-based calibration range once such features leave the field of view of the camera 150. Thus, when a global reference feature or an object feature leaves the field of view of the camera 150, the controller 160 can transition to implementing closed-loop controls to move the end effector 140 to target positions in real space based on outputs of these encoders (or other angular position sensors) with a relatively high degree of locational accuracy near this local calibrated range.

In this variation, while the global reference feature and the object feature remain outside of the field of view of the camera 150, the controller 160 can also: record a video feed (i.e., a sequence of optical images) from the camera 150 while the arm is in motion; implement optic flow techniques to extract position changes and/or velocity values of the camera 150 (and therefore the end effector 140) from the video feed; and continue to recalibrate the angular position sensors in the joints of the arm to real local changes to the pose of end effector 140 in real space based on these optic-flow-derived position changes and/or velocity values extracted from the video feed.

The system 100 can therefore implement these methods and techniques to (re)calibrate the angular position sensors in the arm in real-time while a global reference feature and/or object feature—of known size, geometry, etc.—is in the field of view of the camera 150 and then rely on outputs of these locally-calibrated angular position sensors for tracking the pose of the end effector 140 in real space while such global reference features and/or object features are not detected in the field of view of the camera 150.

The system 100 can execute similar methods and techniques during a calibration routine upon first startup, when a new end effector 140 is installed at the end of the arm, following a crash event, when the system 100 is moved, or at regular intervals (e.g., once per month or once per 100 hours of use); and the controller 160 can (re)calibrate sensors within the arm based on optical data recorded by the camera 150 during a discrete calibration routine accordingly.

2.4 Dynamic Transitions

As shown in FIG. 4, the controller 160 can also execute Blocks of the first method S100 to dynamically switch between: registering motion of the end effector 140 to an object reference frame or to an object feature; registering motion of the end effector 140 to a global reference frame or to a global reference feature; and interpolating a pose of the end effector 140—in a machine, global, or object reference frame—according to outputs of angular position sensors in the arm and a known geometry of the arm based on whether global reference and object features are present in an image output by the camera 150 and whether these global reference and object features are of sufficient resolution. For example, the controller 160 can initially implement closed-loop controls to move the end effector 140 through a preplanned trajectory toward an object keypoint—defined in a machine reference frame—based on outputs of the angular position sensors. Once this global reference feature is detected, the controller 160 can: define a global reference frame based on this global reference feature; project the preplanned trajectory into the global reference frame; and transition to implementing closed-loop controls to move the end effector 140 along the preplanned trajectory toward the object keypoint based on the position of the global reference feature within the field of view of the camera iso. As the end effector 140 moves toward the target object and once an object feature representing the target object is detected in the field of view of the camera 150, the controller 160 can: define an object reference frame; project the preplanned trajectory into the object reference frame; and transition to implementing closed-loop controls to move the end effector 140 along the preplanned trajectory toward the target object based on the position of the object feature in the field of view of the camera 150.

The controller 160 can also calibrate the angular position sensors while registering motion of the end effector 140 to the object feature. Thus, when the end effector 140 nears the target object and the object feature moves out of the field of view of the camera 150 due to offset between the end effector 140 and the camera 150, the controller 160 can transition back to implementing closed-loop controls to move the end effector 140 a final distance into contact with the target object based on outputs of the angular position sensors, now calibrated to the local pose of the end effector 140. Once the end effector 140 engages (e.g., grips, locks into) the target object, the controller 160 can implement closed-loop controls to retract the end effector 140, such as along a second preplanned trajectory defined in a machine reference frame—based on outputs of the angular position sensors. Once the global reference feature, a second object feature, or another target feature representing a target install or release position for the target object is detected in the field of view of the camera 150, the controller 160 can transition to registering motion of the end effector 140 to this feature or to a reference frame located in real space based on this feature.

Therefore, the system 100 can implement Blocks of the first method S100 to transition between registering motion of the end effector 140 to various features based on availability of these features in the field of view of the camera 150, the quality of these features detected in the field of view of the camera 150, and relevance of these features to maintain a high degree of precision in locating the end effector 140 when engaging target objects or other surfaces of interest near the system 100.

3. Arm and Camera

As described above, the base 110 and arm 120 can define a robotic arm 120 including activated joints between beam sections 121, 122 that can be manipulated to move an end effector 140 mounted to the arm 120, such as to the far end of the arm 120 opposite the base 110. Each joint can define one or more actuatable axes driven by an internal actuator 130 (e.g., a servo motor) or by a remote actuator 130, such as a gearhead motor arranged in the base no and coupled to the joint by a set of tensioned cables. The arm 120 can also include one or more sensors in each joint, such as a position sensor (e.g., a rotary optical encoder), a force sensor, a torque sensor, and/or an accelerometer, etc. In one variation, the controller 160 calibrates these sensors—at regular intervals (e.g., once per 100 hours of operation) or in real-time during operation—based on features in the field around the system 100 extracted from images recorded by the camera 150, as described below.

The camera 150 functions as the system's connection to global and/or object reference frames by outputting optical images (e.g., digital photographic images or a video feed) that the controller 160 can then process in (near) real-time to detect a global reference feature or object feature, determine a pose of the end effector 140 relative to this feature, and then drive actuators 130 in the arm 120 to move the end effector 140 to other target positions in real space defined relative to this feature.

The camera 150 is mounted to the arm 120, such as a beam furthest from the base 110, and can include an RGB or infrared, color or monochromatic, CMOS, CCD, or other camera 150 configured to output images of a field ahead of the camera 150. For example, the camera 150 can output digital photographic color images at a frame rate of 24 frames per second, at a frame rate of once per second, or at "keypoints" along a preplanned trajectory executed by the system 100. The system 100 can additionally or alternatively include: a 3D imaging sensor, such as stereoscopic camera 150s, a structured light imaging system, or other depth sensor (e.g., an infrared depth camera 150) configured to output depth images, such as in the form of 3D point cloud images.

However, the system 100 can include any other type of camera 150 or sensor configured to output images of any other type and in any other format. The system 100 can also include multiple cameras or other optical sensors arranged on one or more elements of the arm, and the system 100 can implement methods and techniques described herein based on images recorded by these multiple cameras. For example, the system 100 can implement methods related to registering motion to an object feature based on the position of the object feature detected in the field of view of a first camera mounted at a first joint immediately behind the end effector, and the system 100 can implement methods related to registering motion to a global reference feature based on the position of the global reference feature detected in the field of view of a second camera mounted at a second joint mounted to the same element of the arm but opposite the end effector.

The system 100 (or a remote database 110) can also store empirical intrinsic properties of the camera 150, such as focal length, image sensor format, principal point, lens distortion, and/or entrance pupil (or nodal point). The controller 160 can then access any one or more of these intrinsic properties to correct images received from the camera 150 and/or to transform data extracted from these images into a pose of the end effector 140, a particular joint in the arm 120, or the end effector 140 mounted to the end of the arm 120.

4. Reference Features

In subsequent implementations of the first method S100 executed by the system 100, the controller 160 can detect and track one or more external reference features extant in the system's environment across multiple (e.g., three or more) images recorded at unique poses of the camera 150 (or unique poses of the end effector 140 or the arm generally) in real space.

4.1 Global Reference Feature

Figure 2:
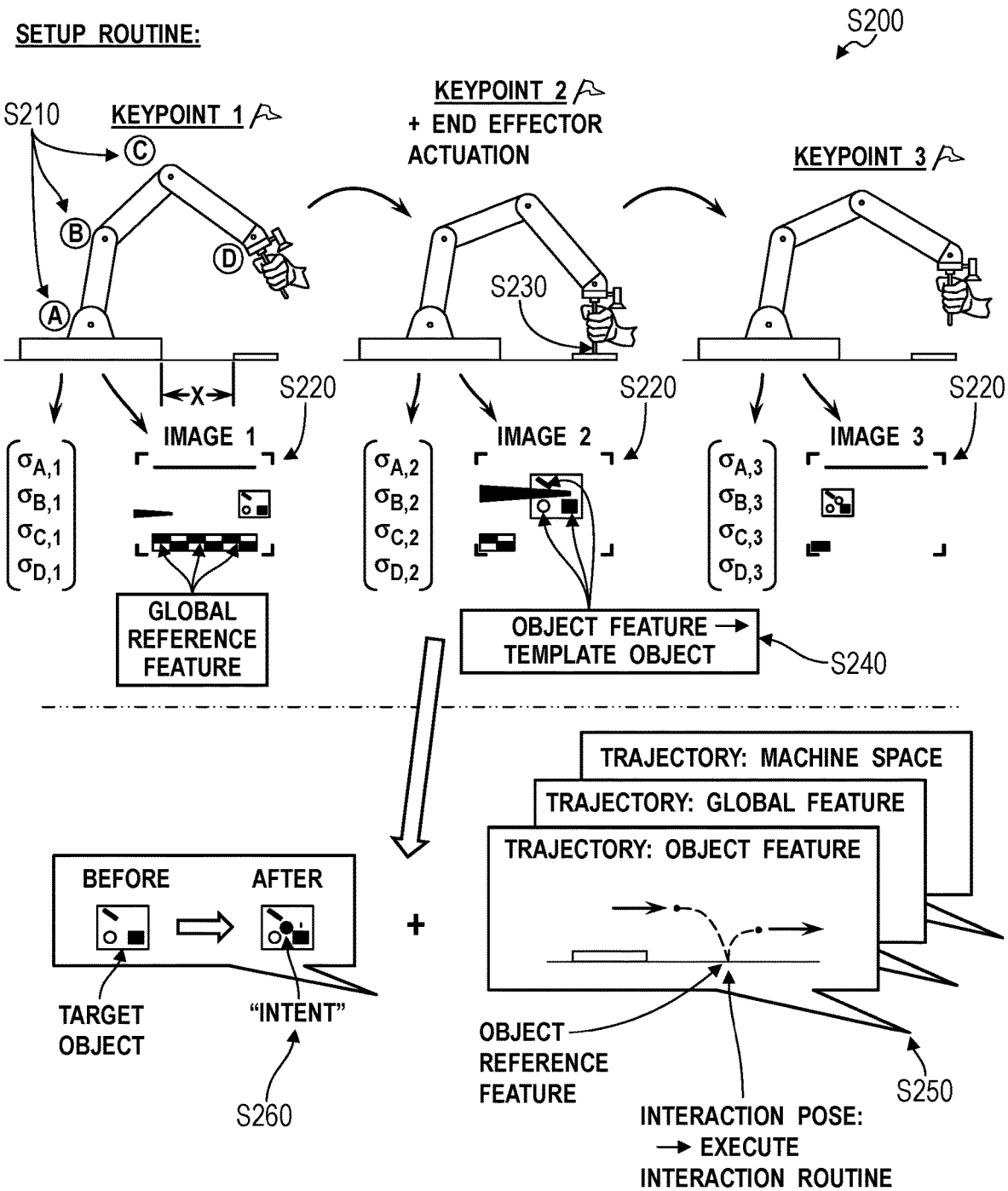
FIG. 2 is a flowchart representation of a second method.

In one implementation shown in FIGS. 1 and 2, the controller 160 detects and tracks global reference features representing common or known features of known size (e.g., length, width) and/or geometry near the system 100 but not representing an object or other surface that the system 100 is programmed or configured to directly contact, move, or otherwise interact with during operation. In particular, the controller 160 can locate a global reference frame according to a known global reference feature when this global reference feature is detected in the field of view of the camera 150, such as when the system 100 sweeps the end effector 140 through a preplanned trajectory toward an estimated location of a target object and before an object feature representing this target object is detected in the field of view of the camera 150. The controller 160 can thus register motion of the end effector 140 to this global reference frame, such as by calculating poses of the end effector 140 within the global reference frame based on the position, size, skew, and orientation of the global reference feature detected in the field of view of the camera 150 and then implementing closed-loop controls to move the end effector 140 along a preplanned trajectory within the global reference feature. The controller 160 can additionally or alternatively calibrate position sensors in the arm based on such changes in the pose of the end effector 140 within the global reference frame over time.

For example, the controller 160 can track the edge of a table on which the system 100 is placed, the perimeter of a light switch cover plate on a wall near the system 100, or other fixed object near the system 100; the controller 160 can handle such a feature as a global reference feature and locate a global reference frame relative to this feature.

Alternatively, the controller 160 can track one or more active or passive optical fiducials of known size and geometry installed on or near the system 100. For example, the system 100 can be arranged on or near a two-dimensional black and white checkerboard mat, and the controller 160 can: implement computer vision techniques to track sizes, geometries, and distortion of black and white regions of the checkerboard map across images recorded by the camera 150 as the end effector 140 moves through a sequence of poses in real space; transform changes in the sizes, geometries, and distortion of these black and white regions of the checkerboard into absolute changes of the pose of the end effector 140 in real space, such as based on a known size and geometry of the checkerboard; and then calibrate position sensors in the arm accordingly, as described below. The controller 160 can also: dewarp an image recorded by the camera 150 occupying a single pose by applying a predefined homography transform customized for intrinsic and extrinsic properties of the camera 150; and then locate a global reference frame relative to the checkerboard detected in the single dewarped image based on a known size and geometry of the checkerboard and the position, size, and skew, etc. of the checkerboard detected in the dewarped image. Alternatively, the controller 160 can aggregate three images recorded by the camera 150 while occupying three different poses (e.g., as the controller 160 drives the end effector 140 through a trajectory) into a three-dimensional sparse map of the environment around the system 100 by aligning features in these images representing the checkerboard and based on known properties of the checkerboard; define a global reference relative to the checkerboard; and calculate a change in pose of the camera 150 (or the end effector 140) when occupying a subsequent pose, such as by calculating a transform that projects features of the checkerboard extracted from an image recorded by the camera 150 in this subsequent pose onto the checkerboard in the three-dimensional sparse map.

In a similar example, the system 100 can further include a passive black and white checkerboard pattern and/or a set of active fiducials (e.g., color or infrared LEDs) patterned across the exterior surface of the housing. The controller 160 can thus implement similar methods and techniques to calibrate sensors in the arm and/or to define a global reference frame based on features—representing this checkerboard pattern and/or these active fiducials arranged on the base—extracted from images recorded by the camera 150.

The system 100 can be preloaded with a model of the global reference feature, and the controller 160 can implement this model to systematically scan images and to confirm whether the global reference feature is present in these images. For example, the system 100 can be loaded with a global reference feature classifier, such as in the form of a neural network or other artificial intelligence, trained on images of the same or similar global reference features, configured to scan an image, and configured to output a binary value for whether the image contains the global reference feature (or a constellation of the global reference features). (Alternatively, the global reference feature classifier can output a confidence score for presence of the global reference feature or the constellation of global reference features in the image, and the controller 160 can handle the image based on whether the confidence score exceeds a preset threshold value.) The global reference feature classifier can therefore be trained on photographic images and/or renderings (e.g., CAD renderings) of the global reference feature—such as a planar or non-planar checkerboard of known size and geometry, a hard feature of a table, floor, or other support structure under the system 100, a pattern (e.g., a grid) applied to a surface on or near the base, etc.—and the controller 160 can implement this global reference feature classifier to detect the presence (and position, orientation, skew) of this known global reference feature in images recorded by the camera 150 throughout operation of the system 100.

However, the controller 160 can implement any other method or technique to detect a global reference feature of any other type and arranged in any other way on or near the system 100. The controller 160 can additionally or alternatively: implement optical flow techniques to track arbitrary, unknown global features across a sequence of images output by the camera 150 and to calculate a velocity or change in pose of the end effector 140; and then calibrate position sensors in the arm accordingly, a described below.

4.2 Object Feature

The controller 160 can implement similar methods and techniques to detect and track an object feature representing a target object that the system 100 is configured or programmed to contact, move, or otherwise manipulate during operation, as in FIGS. 1 and 2. In particular, when an object feature is detected in an image output by the camera 150 and/or when this object feature detected in the image is of sufficient resolution (e.g., "large enough") to reliably define an object reference frame, the controller 160 can locate an object reference frame according to this object feature, such as by virtually locating an origin of the object reference frame on this object feature and aligning axes of the object reference frame to one or more axes of the object feature. The controller 160 can thus register motion of the end effector 140 to this object reference frame, such as by calculating poses of the end effector 140 within the object reference frame based on the position, size, skew, and orientation of the object feature detected in the field of view of the camera 150 and then implementing closed-loop controls to move the end effector 140 along a preplanned trajectory projected into the object reference feature. The controller 160 can additionally or alternatively calibrate position sensors in the arm based on such changes in the pose of the end effector 140 within the object reference frame, such as when the end effector 140 approaches the target object.

The system 100 can be preloaded with a model of the object feature, and the controller 160 can implement this model to systematically scan images and to confirm whether the object feature is present in these images. For example, the system 100 can be loaded with an object feature classifier in the form of a neural network or other artificial intelligence trained on a CAD model, engineering drawings, or images of units of the target object. The controller 160 can scan an image recorded by the camera 150 with the object feature classifier to determine whether the image contains the object feature (or a constellation of object features) representing the target object and repeat this process for each subsequent image recorded by the camera 150 during operation of the system 100.

For example, the target object can include a threaded fastener (e.g., a screw, a nut), a singular component, a subassembly, or a completed assembly; and the controller 160 can detect an object feature—defined by the target object directly—from an image output by the camera 150. The controller 160 can then drive actuators in the arm to engage (i.e., contact) the end effector 140 to the target object. The controller 160 can also trigger the end effector 140 to grasp the target object and then drive the actuators in the arm to move the target object to another position or orientation in a field near the system 100, such as to place the target object over a target location offset from the target object's original position. Alternatively, the controller 160 can drive the actuators in the arm and end effector 140 to retain the target object in its current position while an operator or other instance of the system 100 alters the target object. The controller 160 can also drive the actuators in the arm and end effector 140 to manipulate the target object in its current position, such as by installing a fastener (e.g., a previous target object engaged by the end effector 140 when executing a previous preplanned trajectory) into a bore in the target object or by applying a spot welding tip on the end effector 140 to a target location on the target object and activating the spot welder once the tip has contacted this target location.

4.3 Target Feature

The controller 160 can implement similar methods and techniques to detect and track a target feature within the field of view of the camera 150. For example, the controller 160 can implement a classifier to detect a target feature—representing a fixture, dispenser, or other carrier containing or supporting the target object—in the field of view of the camera 150. As the controller 160 drives actuators in the arm to move the end effector 140 along a preplanned trajectory within a global reference frame, the target feature may come into the field of view of the camera 150. Upon detecting the target feature—which may be directly coupled to the target object, unlike the global reference feature, and may be relatively large compared to the object feature—the controller 160 can define a target reference frame relative to this target feature, project the preplanned trajectory into the target reference frame, and continue to move the end effector 140 along the preplanned trajectory, now in the target reference frame. As the end effector 140 approaches the target object, the object feature may come into the field of view of the camera 150 and/or be of sufficient size to reliably define an object reference frame relative to this object feature. The controller 160 can thus define an object reference frame relative to this object feature, project the preplanned trajectory into the object reference frame, and continue to move the end effector 140 along the preplanned trajectory, now in the object reference frame, until the end effector 140 contacts the target object.

The target feature can therefore represent an intermediate feature that is larger and/or more easily detected by the controller 160 given the resolution of the camera 150. To achieve finer locational accuracy of the end effector 140 in real space as the end effector 140 approaches the target object, the controller 160 can transition from: registering motion of the end effector to the global reference feature; to registering motion of the end effector to the target feature; to registering motion of the end effector to the object feature as these features come into the field of view of the camera 150.

In another example, the target feature can target a release position for the target object—currently engaged (e.g., grasped) by the end effector 140—such as a threaded bore in a second object. In this example, once the end effector 140 engages the target object defining a machine screw, the controller 160 can: retract the end effector 140 and move the end effector 140 along a second preplanned trajectory in a machine reference frame based on outputs of the position sensors; locate a global reference frame and project the second preplanned trajectory into the global reference frame once the global reference feature is detected in the field of view of the camera 150; locate a target reference frame and project the second preplanned trajectory into the target reference frame once the target feature is detected in the field of view of the camera 150; and continue to move the end effector 140 along the preplanned trajectory—now defined in the target reference frame—until the machine screw engages the threaded bore. Once the machine screw engages the threaded bore, the controller 160 can rotate the end effector 140 about an axis of the machine screw while continuing to drive the end effector 140 forward to set the machine screw in the threaded bore. The target feature can therefore represent a target release position of the target object directly or indicate a target release position nearby; and the controller 160 can move the end effector 140 in real space based on the position and orientation of the target feature in the field of view of the camera 150.

5. Calibration Cycle

During a calibration cycle, the system 100 can generate a calibration table that links outputs of position sensors integrated into each joint of the arm to movement of the end effector 140 in six degrees of freedom within a global or object reference frame, as shown in FIG. 1. In particular, position sensors (e.g., optical encoders) in or coupled to joints in the arm may exhibit drift and/or resolution limitations that yield an increasing range of possible locations of the end effector 140 in real space at greater distances from the base of the end effector 140 (e.g., as the arm is extended and the end effector 140 moved away from the base). This range of possible locations of the end effector 140 in real space can further increase as joints in the arm wear over time, thereby reducing the precision (i.e., accuracy and repeatability) with which the system 100 may locate the end effector 140 when relying on outputs of these position sensors to determine the pose of the end effector 140 in machine coordinates.

However, the system 100 can: detect a known feature in an image recorded by the camera 150 installed on or integrated into the arm (or into an end effector 140; track this feature over a sequence of images output by the camera 150 as the arm moves the end effector 140 through a trajectory; calculate a change in the position of the camera 150 relative to this feature (e.g., in a global or object reference frame) over the sequence of images; transform this change in the position of the camera 150 to a change in pose of the end effector 140 relative to the feature based on a known offset from the camera 150 to the end effector 140; track outputs of the position sensors as the end effector 140 moves through this trajectory; and then generate a lookup table or arm model that maps these outputs of the position sensors to the change in pose of the end effector 140 relative to the feature (e.g., within the global or object reference frame). Specifically, during a calibration cycle, the system 100 can automatically calibrate motion of joints in the arm within a machine coordinate system to motion of the end effector 140 in a global or object reference frame based on changes in the position, size, skew, etc. of one or more features tracked across a sequence of digital photographic images—recorded by the camera 150—during motion of the arm, as shown in FIG. 1.

For example, the system 100 can generate a lookup table or an arm model including one joint model per joint or axis of the arm generated during a calibration cycle. The system 100 can later implement these calibration data to: zero a force sensor, a torque sensor, and/or a position sensor in each joint of the arm; and/or calculate target output values of a force sensor, torque sensor, and/or position sensors in each joint of the arm to achieve a target position of an end effector 140 installed at the end of the arm. The system 100 can therefore execute a calibration cycle to automatically "master" or "home" the arm and to automatically calibrate motion of the arm based on features detected in images recorded by a camera 150 mounted to the arm and without necessitating contact with a physical reference object placed near the arm.

5.1 Single Joint Calibration

In one implementation, the controller 160 calibrates one joint in the arm at a time by independently driving the one joint through its range of motion and processing images recorded by the camera 150 at select keypoints in this range of motion. In this implementation, the controller 160 can target a joint offset distance (e.g., 5° in rotation) within a range of motion of a selected joint and trigger the camera 150 to record an image at keypoints offset radially by this target joint offset distance as the joint traverses its range of motion. For example, the target joint offset distance can include a subset of the range of motion of the joint for which a suitable degree of confidence exists that an optical feature (e.g., a global reference feature, an object feature, a target feature, etc.) detected in an image recorded at an initial position of the joint will also be shown in a second image recorded at a second position of the joint offset from the initial position by the target joint offset distance.

During a calibration cycle for the selected joint, the controller 160 can: "lock" all other joints in the arm (e.g., by implementing closed-loop controls to maintain the position of these other joints based on position data read from position sensors in these other joints); record a first keypoint image at an initial position; implement closed-loop controls to move the joint from an initial position by the target joint offset distance based on position values read from a first position sensor (e.g., an optical encoder) coupled to or arranged in the first joint; and then record a second keypoint image once the joint reaches the second position offset from the first position by the target joint offset distance. The controller 160 can repeat the foregoing process to move the joint to a third position offset from the second position by the target joint offset distance, to capture a third keypoint image at the third position.

The controller 160 (or an external computer system, such as a desktop computer or a remote server coupled to the system 100) can then implement computer vision techniques to identify and track like features in the first keypoint image and the second keypoint image and to combine the first, second, and third keypoint images into a three-dimensional sparse map—such as a 3D point cloud or other three-dimensional representation of the system's environment—represented in overlapping areas of the first, second, and third keypoint images based on known intrinsic properties of the camera 150.

The controller 160 can also: implement feature detection and tracking to track a common feature (e.g., a global reference feature, an object feature, and/or a target feature, etc.) across the first keypoint image and the second keypoint image or implement optical flow techniques to track net movement of pixels between the first keypoint image and the second keypoint image; and transform differences in the position of the feature (or pixels) between the first and second keypoint images—given a known scale (e.g., dimension) and geometry of the feature extracted from the three-dimensional sparse map—into a change in the position of the entrance pupil of the camera 150 in real space between the initial position and the second position. Based on a known position of the camera 150 (or the camera's entrance pupil) relative to the joint, the controller 160 can transform this calculated change in the position of the camera's entrance pupil in real space into a change in the arcuate position of the joint in real space from the initial position to the second position. By calculating a real change in the position of the selected joint between the first position and the second position based on features extracted from a sequence of images recorded by the camera iso, labeling this camera iso-based distance value as true, and then storing this camera iso-based distance for the real change in position of the joint with position values read from the position sensor in the joint between the first and second positions, such as in a lookup table or virtual model of the arm, the controller 160 can calibrate the position sensor in the joint to the real position of the joint over this subset of the joint's range of motion to optical data recorded by the camera 150.

The controller 160 can repeat the foregoing process to calibrate outputs of the position sensor in the joint between the second and third positions based on optical data captured in the second and third keypoint images and to update the lookup table or virtual model of the arm accordingly. Furthermore, the controller 160 can step the joint through its full range of motion by the target joint offset distance, capture a keypoint image at each of these steps, and calibrate the position sensor in the joint between each of these steps, thereby calibrating the full range of motion of the joint. In particular, the system 100 can repeat the foregoing process for other positions throughout the range of motion of the joint to characterize the full range of motion of the joint based on keypoint images record by the camera 150 throughout this range of motion.

In one example in which the selected joint includes an optical encoder defining 1000 discrete points or "ticks," the controller 160 can define a target joint offset distance of 7.2°—or 20 ticks on the encoder—between keypoints along the range of motion of the joint. The controller 160 can then implement the foregoing process to record keypoint images at a first and second keypoint within the joint's range of motion, to track features between these two keypoint images, and to determine that the real change in angular position of the joint between the first keypoint and the second keypoint is 7.3°. The controller 160 can thus update a lookup table or virtual model of the arm to indicate that 20 ticks of the encoder—between the first and second positions—yields 7.3° of motion in the first joint 123 rather than a predicted 7.2°. The controller 160 can also interpolate these 20 ticks between the first and second position of the joint to determine that each tick between the initial and second positions represents an angular offset of 0.365° rather than a nominal 0.360° and update the lookup table or virtual model of the arm accordingly. The controller 160 can repeat this process for each other 7.20° target joint offset distance throughout the range of motion of the joint.

However, the system 100 can implement any other methods or techniques to transform optical data recorded by the camera 150 at various positions of the arm into absolute changes in the pose of the end effector 140 in real space and to calibrate position sensors in the arm accordingly based on the optically-derived absolute change position values.

5.2 Complete Arm Calibration

Once the controller 160 characterizes motion of a first joint 123 in the arm and updates a lookup table or joint model of the arm accordingly, as described above, the controller 160 can repeat this process for each other joint in the arm sequentially and independently of other joints in the arm in order to fully characterize the arm and to calibrate all motion sensors in the arm.

In one implementation, the system 100 first calibrates a joint furthest from the base (e.g., the second joint) since motion of this furthest joint may yield least overall or total motion of the arm. The controller 160 can calibrate this furthest joint initially within a narrow first subset of its range of motion (e.g., 10°), then expand the tested range to a second subset (e.g., to 30°) of the joint's range of motion and recalibrate the joint over this second subset once motion within the first subset is approved (e.g., if no crash event occurs within the first subset), and then expand the tested range to a third subset (e.g., to 90°) of the joint's range of motion and recalibrate the joint over this third subset once motion within the second subset is approved, etc. The controller 160 can thus increase a calibrated range of the furthest joint as confidence that articulation of the first joint 123 will not result in a crash or damage to an actuator or linkage increases. Once the furthest joint is calibrated, the controller 160 can implement similar methods and techniques to calibrate a next-furthest joint from the base, etc.

In the implementation described above in which the system 100 includes a passive or active optical fiducial arranged on the base, the system 100 can be shipped with the arm in an initial position with the optical fiducial on the base in the field of view of the camera 150 such that a first set of images recorded by the camera 150—when the system 100 is first activated and the furthest joint is moved during an initial startup period—depict the optical fiducial. The controller 160 can thus calculate real dimensions of the environment around the system 100 from these initial images in order to generate a dimensionally-accurate three-dimensional sparse map of the system's environment before calibrating each joint in the arm based on the three-dimensional sparse map. Furthermore, when the system 100 is shut down, such as when the system 100 is turned off when not in use or in preparation for transport (e.g., to another position along the same assembly line or to another assembly line), the controller 160 can drive joints in the arm back to this initial position with the optical fiducial on the base in the field of view of the camera 150 such that, when the system 100 is later reactivated, the controller 160 can repeat the foregoing process to generate a dimensionally-accurate three-dimensional sparse map of the system's new environment before recalibrating each joint in the arm.

5.3 Slop

In one variation, when transforming differences in the position of a feature between the first and second keypoint images into a change in the position of the entrance pupil of the camera 150 in real space, the controller 160 may determine that the entrance pupil of the camera 150 has rotated about a primary axis of the first joint 123 but also rotated about a primary axis of a second joint 124 in the arm. The controller 160 can: label rotation of the entrance pupil of the camera 150 about the second joint 124 as slop in the second joint 124 at the current position and throughout the range of motion from the initial position and the second position; and then write a quantitative value representing this slop and where in the range of motion of the first and second joints that this slop in the second joint 124 occurs.

For example, articulation of the first joint 123 in a first direction over a subset of the range of motion can move a mass at the end of the arm away from the base and may load or tension the second joint. This increased load on the second joint 124 may yield subtle deflection of the second joint, that is "slop", in the second joint 124 as a function of the position of the first joint. Similarly, when the first joint 123 returns the mass at the end of the arm back toward the base, total detected slop in the second joint 124 may lessen. The controller 160 can: detect this deflection of the second joint 124 over this subset of the range of motion of the first joint 123 based on differences in the position and geometry of a like feature between two keypoint images; and then store this characterization of the second joint 124—as a function of the position of the first joint 123—in the lookup table or virtual model of the arm. When the controller 160 later executes a trajectory that moves the first and second joints of the arm through a similar range of motion, the controller 160 can pre-load the second joint 124 against this measured slop in the second joint 124 in order to locate the end of the arm to a greater degree of precision (i.e., more repeatably and with less variation from the target trajectory across these ranges of motion).

Therefore, though joints in the arm may exhibit relatively large amounts of "slop" or deflection as a function of positions of other joints in the arm, the controller 160 can compensate for such excessive slop in the joints by: generating a model of each joint as a function of positions of other joints in the arm based on features tracked throughout sequences of keypoint images recorded by the camera 150 during a calibration cycle; and then actively articulating each joint in the arm against such slop—defined in the joint models as functions of positions of each joint in the arm—as the system 100 executes a target trajectory.

Furthermore, the load on a joint in the arm throughout its range of motion may be a function of the size (i.e., mass) and geometry (e.g., center of gravity) of an end effector 140 installed on the end of the arm. The controller 160 can therefore repeat the foregoing methods and techniques to generate one joint model per joint specific to the particular end effector 140 installed on the end of the arm; when the particular end effector 140 is installed on the arm the controller 160 can retrieve and implement joint models specific to this particular end effector 140. Similarly, the load on a joint in the arm throughout its range of motion may be a function of the size and geometry of an object (e.g., a screw, a component in an assembly) selected or manipulated by the particular end effector 140 installed on the end of the arm. The controller 160 can therefore generate and implement joint models specific to one particular end effector 140 interfacing with one particular type of physical object for each joint of the arm. For example, when executing an operation in which the arm repeatedly selects and releases units of an object type (e.g., screws, an assembly component) of sufficient mass to materially alter the load on a joint in the arm, the controller 160 can: generate and implement a first set of joint models defining real motion of each joint throughout its range of motion as a function of positions of other joints in the arm when the end effector 140 is not interfacing with a unit of the object type; and generate and implement a second set of joint models defining real motion of each joint throughout its range of motion as a function of positions of other joints in the arm when the end effector 140 is interfacing with a unit of the object type.

The controller 160 can implement the foregoing methods and techniques to characterize slop in each joint of the arm and can then: prompt an operator to service the system 100, such as by manually replacing or adjusting joints in the arm; and/or disable the system 100 when measured slop exceeds a threshold slop in one or more joints. However, the controller 160 can implement any other methods or schema to characterize and handle slop in the arm.

5.4 Intermittent Recalibration

The controller 160 can execute the foregoing processes to recalibrate machine-coordinate outputs of sensors in the arm to changes in the pose of the end effector 140 (or interface surface or other reference surface on the arm) in a feature-based reference frame, such as on a regular interval of once per month, once per 100 hours of operation, after every crash event, after a service event, and/or following installation of a different end effector 140 on the arm.

6. Real-Time Calibration

In another variation, the controller 160 calibrates machine-coordinate outputs of sensors in the arm to changes in the pose of the end effector 140 in a feature-based reference frame in real-time while the system 100 executes a preplanned trajectory, such as described below, as shown in FIG. 1. Generally, in this variation, the controller 160 feeds image-based data—instead of or in addition to machine-coordinate position data from position sensors in the arm—into a control loop to control the position of each joint while the arm traverses an end effector 140 installed on the end of the arm through a preplanned trajectory. In particular, the controller 160 can: move the arm through a sequence of three-dimensional keypoints defined by a preplanned trajectory, such as in a machine, global, or object reference frame based on available sensor data; trigger the camera 150 to record an image once the arm (e.g., the end effector 140) reaches each of these keypoint positions; calibrate outputs of the position sensors (and other sensors in the arm) in (near) real-time based on changes in the pose of the arm determined from changes in positions of an optical feature over this sequence of images.

In one implementation, the computer system can calculate the pose of the end effector 140 (e.g., an interface surface defined by the end effector 140)—at a particular time and relative to an optical feature (e.g., the global reference feature, the object feature) near the system 100—directly from a single optical image recorded at (approximately) the particular time based on: the position, orientation, skew, etc. of the optical fiducial in the image; a known geometry of the optical feature, as described below; and a known offset between the camera 150 and the interface surface. In particular, by detecting a known optical feature in an image camera 150 and extracting pose information directly from this image based on a known geometry of the optical feature and based on a known offset between the camera 150 and the end effector 140, the controller 160 may complete a pose calculation for the end effector 140 relatively rapidly and with increasing locational accuracy as the end effector 140 approaches this optical feature. By repeating this process as the actuators drive the end effector 140 through the preplanned trajectory, the controller 160 can: track outputs of position sensors in the arm; calculate changes in feature-based poses between consecutive sampling intervals; and calibrate the position sensors accordingly.

Alternatively, the computer system can fuse these images recorded over a sequence of keypoints occupied by the end effector 140 into a three-dimensional sparse map (e.g., a 3D point cloud) of static surfaces—such as a work table and various active and/or passive fiducials—around the system 100, such as by implementing 3D image stitching techniques and a fiducial of known size and geometry, as described above. The controller 160 can then compute the pose of the end effector 140 (or the camera 150, or one or more joints in the arm) in real space—such as in a feature-based reference frame—at a subsequent time based on a transformation that maps features identified in an image recorded at this time to like features in the three-dimensional sparse map. In this implementation, the controller 160 can compare geometries of features identified in an image recorded by the camera 150 to geometries of like features represented in the sparse map—substantially in real-time during execution of the preplanned trajectory—to determine the camera's position in real space in a feature-based reference frame at the time the image was recorded and then implement a known offset between the end effector 140 and the camera 150 to transform this camera 150 position into a pose of the end effector 140 (or an interface surface on the end effector 140) in the feature-based reference frame. For example, upon receipt of a new image, the controller 160 can: implement object recognition techniques to identify a feature (e.g., an optical fiducial) in the new image also extant in the sparse map; calculate a transformation that maps this feature in the new image to the size and geometry of the like feature in the sparse map; and calculate a real position of the entrance pupil of the camera 150 relative to the feature in real space (e.g., in a global reference frame) based on (the inverse of) the transformation; and calculate the pose of the interface surface of the end effector 140 installed on the arm (e.g., a screwdriver tip) based on the real position of the entrance pupil of the camera 150 relative to the feature in real space and a known pose of the interface surface relative to the entrance pupil of the camera 150. By repeating this process over a sequence of images, the controller 160 can track changes in the pose of the interface surface in the global reference frame over time and apply these changes to a lookup table or arm model for position sensors in the arm, thereby calibrating outputs of these sensors in machine coordinates to changes in the pose of the interface surface (within a small local volume in real space) in the global reference frame.

The controller 160 can execute any of the foregoing processes for each image recorded by the camera 150—such as at a frame rate of 24 Hz or 1 Hz—when executing a preplanned trajectory in order to regularly recalculate the pose of the end effector 140 in real space relative to an optical feature or relative to a reference frame defined according to this optical feature in real space around the system 100. Furthermore, when executing a preplanned trajectory, the controller 160 can implement closed-loop controls to reposition joints of the based on deviations of the real pose of the interface surface from the preplanned trajectory—in a feature-based reference frame—rather than based on position, force, and/or torque values read from sensors in the arm.

Alternatively, the controller 160 can: intermittently trigger the camera 150 to record an image at a first time; implement the foregoing methods and techniques to determine the real pose of the end effector 140 in a feature-based reference frame at the first time; and project a first segment of the preplanned trajectory—defined in the feature-based reference frame—into machine coordinates, such as to define a sequence of keypoints in machine coordinates along this segment of the preplanned trajectory. The controller 160 can then regularly read position, force, and/or torque data from sensors integrated into the arm (e.g., a rate of 20 Hz) and implement closed-loop controls to sweep the end effector 140 through this sequence of keypoints in machine coordinates. As the end effector 140 reaches the end of this first segment of the preplanned trajectory, the controller 160 can trigger the camera 150 to record a second image and repeat this process for a second segment of the preplanned trajectory. In this implementation, the controller 160 can segment the preplanned trajectory into length proportional to a speed of the end effector 140 in real space, inversely proportional to a distance of the end effector 140 from an object keypoint or other terminus of the preplanned trajectory, etc.

However, the controller 160 can implement any other method or technique to calibrate machine-coordinate outputs of position sensors in the arm to changes in the pose of the end effector 140 in a feature-based reference frame in real-time while the system 100 executes a preplanned trajectory. By regularly (e.g., intermittently or continuously) recalibrating motion of the end effector 140 in machine coordinates to motion of the arm in a feature-based reference frame, the controller 160 can locate the end effector 140 along a preplanned trajectory in a feature-based reference frame based on values output by position sensors in the arm—in machine-coordinates—when such features are not in the field of view of the camera 150 and/or between images recorded by the camera 150.

7. Global Reference Feature Registration

In one variation, the controller 160 tracks the position of a known global reference feature in the field of view to the camera 150 and registers motion of the end effector 140 (or the interface surface) directly to this global reference feature, as shown in FIGS. 1 and 2.

In this variation, the system 100 can: record a first optical image through the optical sensor—arranged proximal a distal end of the robotic arm proximal the end effector 140—at a first time (e.g., when occupying a first pose at the first time) in Block Silo; detect a global reference feature in a first position in the first optical image in Block S120; virtually locate a preplanned trajectory relative to the first position of the global reference feature in the first optical image in Block S130 in response to detecting the global reference feature in the first optical image, wherein the preplanned trajectory defines an object keypoint representing an estimated location of a target object within range of the end effector 140; drive the set of actuators within the robotic arm to move the end effector 140 along the preplanned trajectory—virtually located relative to the global reference feature—toward the object keypoint in Block S140; and repeat this process over time, such as at predefined keypoints or at a regular interval, until the end effector 140 has fully traversed the preplanned trajectory or until a target object or target feature, etc. is detected in the field of view of the camera 150.

7.1 Preplanned Trajectory

The controller 160 can therefore access and load a preplanned trajectory that represents a target three-dimensional path to be traversed by the end effector 140 (or interface surface, camera 150, or joint(s) in the arm, etc.) in real space, such as defined in a global reference frame, an object reference frame, and/or a machine reference frame.

In one example, the controller 160 can: calculate a location of the global reference frame relative to a global reference feature detected in the field of view of the camera 150 based on a known size and geometry of the global reference feature; calculate the pose of the end effector 140 relative to the global reference feature further based on a known offset between the camera 150 and the end effector 140; implement closed-loop controls to drive actuators in the arm to move the end effector 140 along a preplanned trajectory—defined in the global reference frame—based on differences between the feature-based pose of the end effector 140; and repeat this process based on the position of the global reference feature detected in the field of view of the camera 150 until the end effector 140 reaches the terminus of the preplanned trajectory or until a target object or target feature, etc. comes into the camera's field of view. In another example, the preplanned trajectory can be defined as (e.g., include) a sequence of template images each representing a target position, size, orientation, and skew of the global reference feature in the field of view of the camera 150 at a particular keypoint along the preplanned trajectory.

In yet another example, the controller 160 can: detect the global reference feature in an image output by the camera 150 while the end effector 140 occupies a particular keypoint; calculate a transform that maps the global reference feature detected in this image onto a representation of the global reference feature in a template image of a next keypoint along the preplanned trajectory; and then implement closed-loop controls—based on outputs of position sensors in the arm—to drive each joint into a position corresponding to this transform and thus achieve a next pose represented by this next keypoint. (In this example the controller 160 can also implement calibration or other regression techniques, as described above, to develop and refine a model for interpreting such a transform as a target angular offset for each joint in the arm—from a current keypoint to a next keypoint—based on a positional difference between the global reference feature detected in a next image recorded at the next keypoint and the global reference feature represented in the template image corresponding to this next keypoint.)

In one implementation, the system 100 generates the preplanned trajectory based on manual manipulation of the arm, as shown in FIG. 2. In one example in which the system 100 is arranged on a table with a global reference feature (e.g., a checkerboard) applied to the base, to a table or other surface on which the system 100 is mounted, or otherwise arranged near the system 100, an operator may set the system 100 in a "record mode" in which the controller 160 "unlocks" joints in the arm and records position sensor and/or optical data during manual manipulation of the arm during a setup routine. The operator can then move the end effector 140 in real space, such as: from a template object location at which the end effector 140 engages a template target object to a template target location in which the end effector 140 releases the template target object and/or executes a release routine to place or install the template target object in the template target location; and back to the template object location. As the operator manually manipulates the end effector 140 from a first pose (e.g., the template object location) to a second pose (e.g., the template target location) in real space, the controller 160 can record a sequence of keypoint images, such as automatically at a preset rate (e.g., 24 Hz, 2 Hz), per each linear distance traversed by the end effector 140 (e.g., per ten millimeters traversed), proportional to the speed of the end effector 140, or in response to receipt of a trigger—such as a button on the arm or other local interface selected manually by the operator—indicating a keypoint pose. Upon completion of the setup routine, the controller 160 (or a remote computer system) can: extract positions of the global reference feature from the sequence of keypoint images; and compile positions of the global reference feature—detected in the sequence of keypoint images—into the preplanned trajectory extending from the first pose to the second pose in Block S250, as shown in FIG. 2.

In the foregoing example, for each keypoint image recorded during the setup routine, the controller 160 (or the remote computer system) can: locate an origin of a three-dimensional global coordinate system in a fixed position relative to the global reference feature detected in a keypoint image and define a global reference frame in this keypoint image by projecting the three-dimensional global coordinate system onto the origin based on an orientation and skew of the global reference feature detected in this keypoint image and predefined global reference frame rules; calculate a position of the camera 150 in real space within this global reference frame based on the position, size, orientation, and skew of the global reference feature in the corresponding keypoint; and transform this position of the camera 150 into a pose of the end effector 140 (or interface surface) within the global reference frame based on a known static offset or a dynamic offset between the camera 150 and the end effector 140 (e.g., based on an output of position sensors in joints between the camera 150 and the end effector 140). The controller 160 (or the remote computer system) can compile these poses of the end effector 140—in the global reference feature—into the preplanned trajectory in the global reference frame. During operation, the controller 160 can then: access a first image recorded by the camera 150 while the end effector 140 occupies a first pose in Block S110; detect the global reference frame in a first position in the first image in Block S120; calculate a first offset—in the global reference frame—between the first position of the global reference feature in the first optical image and a first keypoint position of the global reference feature in a first keypoint image in the preplanned trajectory in Block S130; then drive the set of actuators to reduce this first offset and to move the end effector 140 toward the terminus of the preplanned trajectory in the global reference frame in Block S140; and repeat this process for each subsequent keypoint image in the preplanned trajectory.

Alternatively, the controller 160 (or the remote computer system) can extract the position, size, orientation, and skew, etc. of the global reference feature from each keypoint image and compile these values to define the preplanned trajectory in the global reference frame. (Similarly, the controller 160 can store these keypoint images directly as template images that the controller 160 attempts to match in the field of view of the camera 150 when traversing the end effector 140 from the first pose to the second pose.) During operation, the computer system can: access a first image recorded by the camera 150 while the end effector 140 occupies a first pose in Block S110; detect the global reference frame in a first position in the first image in Block S120; calculate a transform that maps the position, scale, skew, and orientation of the global reference feature detected in the first optical image to the position, scale, skew, and orientation of the global reference feature in a first keypoint image in Block S130; convert the transform into movement of joints in the arm based on a motion model of the arm (such as locally calibrated according to methods and techniques described above) in Block S140; and then drive the set of actuators according to these movements in Block S140.

The controller 160 (or the remote computer system) can similarly: scan keypoint images recorded during the setup routine for known object features and target features; define corresponding object and target reference frames in keypoint images in which these features were detected; calculate poses of the end effector 140 within these object and target reference frames; and store these poses in preplanned trajectory sets defined in these object and target reference frames. The controller 160 can thus extract multiple sibling preplanned trajectories from one sequence of keypoint images recorded during one setup routine. The controller 160 can also store positions or other values output by position sensors in the arm during the setup routine and generate yet another preplanned trajectory in the machine reference frame for this setup routine. By defining the preplanned trajectory in these distinct references frames, the controller 160 can transition between registering motion of the end effector 140 to sensor data that is most relevant to the system's current task, as described below. These preplanned trajectories defined in difference reference frames may also exhibit redundancy, and the controller 160 can additionally or alternatively register motion of the end effector 140 in a primary reference frame and confirm offsets between the end effector 140 and a next interaction position in a primary reference frame based on a similar offset calculated in a secondary reference frame, such as when both the global reference feature and the object feature are detected in one image.

Various methods executable by the system 100 to generate a preplanned trajectory are described below.

7.2 Global Reference Frame and Joint Actuation

As described above, the controller 160 can trigger the camera 150 to record images in Block S110, such as a preset frame rate or when the controller 160 determines that the end effector 140 has reached a next keypoint by interpolating a pose of the end effector 140 based on outputs of the position sensors since the end effector 140 occupied a preceding keypoint in the preplanned trajectory. The controller 160 can then process these images in (near) real-time to detect the global reference feature, to define (e.g., virtually locate) the global reference frame in real space, and/or to register the preplanned trajectory to the global reference feature detected near the system 100.

In one implementation, upon receipt of an image from the camera 150, the controller 160: implements edge detection, feature detection, object recognition, and/or other computer vision methods and techniques to extract features from an image recorded in Block S110; aggregates these features into a constellation of features (e.g., a "fingerprint" of the field of view of the camera 150); confirms that the constellation of features extracted from the image represents the global reference feature based presence of similar types and relative positions of features in the constellation and features defined in a virtual model of the global reference feature; and locates an origin of the global reference frame on (or otherwise relative to) this confirmed global reference feature.

The controller 160 can then: calculate a transform that maps (e.g., rotates, translated, skews, and/or scales) features defined by the model of the global reference feature onto corresponding features in the constellation of features extracted from the image; virtually orient axes of the global reference frame in the field of view of the camera 150 based on the transform (e.g., based on the orientation, skew, and size of the global reference feature in the camera 150 field of view, as represented by the transform) in Block S130; and calculate the current pose of the end effector 140 within this global reference frame based on this transform and a known transform defining an offset between the camera 150 and the end effector 140. By accessing the preplanned trajectory that defines a three-dimensional target path for the end effector 140 within the global reference frame (and that terminates at an object keypoint defined within the global reference frame) (or by projecting the preplanned trajectory into the global reference frame) in Block S130, the controller 160 can then: calculate an offset between the preplanned trajectory (e.g., a next keypoint in the preplanned trajectory) and the current pose of the end effector 140 within the global reference frame; transform this offset into target changes in the position of each joint in the arm, such as based on a motion of arm calibrated over a locate range of motion as described above; and then implement closed-loop controls—based on outputs of the position sensors in machine coordinates—to drive actuators in this arm to reduce this offset between the end effector 140 and preplanned trajectory (e.g., the next keypoint) in Block S140.

Furthermore, because joints in the arm may occupy various positions for a any singular pose of the end effector 140, the controller 160 can: read or track the angular position of each joint in the arm based on outputs of position sensors coupled to these joints; calculate an actuation direction for each joint in the robotic arm based on the orientation of each joint in the robotic arm and the current offset between the end effector 140 and the preplanned trajectory (e.g., a next keypoint or the object keypoint); and then drive the set of actuators according to actuation directions for corresponding joints in the robotic arm to reduce this offset. The controller 160 can thus move the end effector 140 from its current pose back onto the preplanned trajectory and along the preplanned trajectory toward an object keypoint at the terminus of the preplanned trajectory within the global reference frame based on the position of the global reference feature in the field of view of the camera 150 and based positions of joints in the arm in machine coordinates.

As the end effector 140 moves relative to the global reference feature in real space, the controller 160 can repeat the foregoing process to track the position and orientation, etc. of the global reference feature in subsequent images recorded by the camera 150, recalculate the pose of the end effector 140 within the global reference frame registered to the global reference feature, and to drive actuators in the arm to move the end effector 140 along this preplanned trajectory in the global reference frame.

8. Object Feature Registration

In another variation, the controller 160 dynamically registers the arm directly to a target object in real space—and not to machine coordinates—when actuating the arm in preparation to interface with the target object, as shown in FIG. 3. Generally, in this variation, the controller 160 implements methods and techniques similar to those described above to: capture an image; identify an object feature—representing a target object with which the system 100 is programmed or configured to interface with—in this image; transform the size and geometry of this feature in the image into a pose of the end effector 140 (or camera 150, joint, etc.) relative to the target object or into an object reference frame located relative to the object feature; and to register motion of the arm in real space to this target object. For example, while moving the end effector 140 through the preplanned trajectory defined in the global reference frame, the controller 160 can: access a second image recorded by the camera 150 in Block 150; detect an object feature—representing a known target object—in a second position in the second image in Block S160; virtually align an object keypoint of the preplanned trajectory to the object feature in the second optical image in response to detecting the object feature in the second optical image; and then drive the set of actuators to move the end effector 140 along the preplanned trajectory, virtually aligned to the object feature, toward the object feature, thereby registering motion of the end effector 140 to the target object as the system 100 prepares to engage the target object.

8.1 Object Feature Detection and Object Reference Frame

In one implementation described above, the controller 160 (or remote computer system): accesses a virtual model of the target object; extracts a unique constellation of features from the virtual model; and associates the unique constellation of features with the target object. Upon receipt of an image from the camera 150 in Block S150, the controller 160 can: extract a set of features from the second optical image; and implement edge detection, feature detection, object recognition, and/or other computer vision methods and techniques to match this set of features extracted from the second image to the unique constellation of features representing the target object in order to identify the target object in the second image.

The controller 160 can then implement methods and techniques described above to locate an origin of the object reference frame on (or relative to) the object feature; to align axes of the object reference frame in real space to the object feature; and to calculate the current pose of the end effector 140 in the object reference frame. The controller 160 can also load the preplanned trajectory defined in the object reference frame, as described above. Alternatively, the controller 160 can project the preplanned trajectory from the global reference frame to the object reference frame, such as by: locating the object keypoint defined at the terminus of the preplanned trajectory on the object reference frame; and minimally translating, rotating, stretching, and/or skewing the preplanned trajectory to align a current keypoint of the preplanned trajectory to the current pose of the end effector 140 in the object reference frame, thereby preserving the approach path and end effector 140 orientation as the end effector 140 approaches the target object. The controller 160 can thus project the preplanned trajectory from the global reference frame into the object reference frame by redefining the preplanned trajectory from a current preplanned trajectory adjacent the current pose of the end effector 140 to the object keypoint aligned to the object feature in the field of view of the camera 150.

The controller 160 can then drive the set of actuators to move the end effector 140 onto the preplanned trajectory virtually aligned to the object feature (e.g., in the object reference frame); and drive the set of actuators to move the end effector 140 along this predefined preplanned trajectory in the object reference frame toward the target object. For example, in Block S180, the controller 160 can: calculate a pose of the end effector 140 within the object reference frame based on the position, skew, orientation, and size of the object reference feature in the second optical image; calculate a second offset between the second pose and the preplanned trajectory in the object reference frame; and then drive the set of actuators within the robotic arm to reduce the second offset, thereby moving the end effector 140 toward the target object.

The controller 160 can repeat this process over time as the end effector 140 approaches and then engages the target object at the terminus of the preplanned trajectory (or until the object feature moves outside the field of view of the camera iso).

9. Target Feature Engagement

The controller 160 can implement methods and techniques similar to those described above to register motion of the end effector 140 to a target feature in the field of view of the camera 150, such as by: locating a target reference frame based on a position, orientation, size, and skew of the target feature in an image recorded by the camera 150; locating a target keypoint of a second preplanned trajectory on (or relative to) the target feature; projecting the second preplanned trajectory into the target reference frame accordingly; and moving the end effector 140 along the preplanned trajectory defined in the target reference frame until the end effector 140 reaches the target keypoint.

10. Reference Frame Transition

As described above, the controller 160 can transition between reference frames based on availability of sensor data most relevant to the current task executed by the system 100, such as: a global reference frame when moving between—and some distance away from—a target object and a target release position for the target object; an object reference frame when approaching a target object; a target reference frame when approaching a target release position for the target object; and a machine reference frame when global reference, object, and target features are not detected in the field of view of the camera 150.

For example, the controller 160 can locate a first virtual coordinate system on a first target object (or on a particular surface, edge, corner, center, or target other feature on the first target object) based on detection of the first target object throughout a sequence of images recorded by the camera 150 and implement this first virtual coordinate system to control motion of joints in the arm as the system 100 approaches and engages the first target object (or the first target feature) during a first operation. During a subsequent operation in which the system 100 engages a second target object (or a second target feature on the second target part), the system 100 can discard the first virtual coordinate system, locate a second virtual coordinate system on the second target object based on detection of the second target object throughout a subsequent sequence of images recorded by the camera 150, and implement this second virtual coordinate system to control motion of joints in the arm as the system 100 approaches and engages the second target object (or the second target feature) during a subsequent operation. The system 100 can thus define and cycle through various target-object-based coordinate systems based on the target object with which the system 100 is currently designated to interface.

10.1 Global Reference Frame to Object Reference Frame

In one implementation shown in FIG. 1, the controller 160: accesses a first image recorded by the camera 150 at a first time in Block S110; extracts a first constellation of features from the first image; calculates a first confidence that the first constellation of features represents the global reference feature, such as based on a predefined model of the global reference feature known to exist in a field near the system 100 as described above; calculates a second confidence that the first constellation represents the object feature, such as based on a predefined model of the object feature of a target object that the system 100 is currently configured to interface as described above; detects presence of the global reference feature in the field of view of the optical sensor at approximately the first time in Block S120 in response to the first confidence exceeding a threshold value; and detects absence of the object feature in the field of view of the optical sensor at approximately the first time in response to the threshold value exceeding the second confidence. The controller 160 can then virtually align the preplanned trajectory relative to the global reference feature in Block S130 in response to detecting presence of the global reference feature and detecting absence of the object feature in the field of view of the optical sensor. While the controller 160 can continue to register motion of the end effector 140 to this global reference feature while this known global reference feature is detected in the field of view of the camera 150 and while the object feature is absent the camera 150 field of view.

Later, while the controller 160 drives actuators in the arm to move the end effector 140 along the preplanned trajectory in the global reference frame, the controller 160 can: access a second image recorded by the camera 150 at a second time in Block S150; extract a second constellation of features from the second optical image; calculate a third confidence that the second constellation represents the global reference feature; and calculate a fourth confidence that the second constellation represents the object feature. Like the first image, if the third confidence exceeds the threshold value, the controller 160 can determine that the global reference feature is present in the field of view of the optical sensor at approximately the second time. However, if the fourth confidence exceeds the threshold value, the controller 160 can: determine that the object feature is present in the field of view of the optical sensor at approximately the second time; and automatically transition to registering motion of the end effector 140 to the object feature—such as by virtually realigning the object keypoint of the preplanned trajectory to the object feature as described above—in response to detecting presence of the object feature in the field of view of the optical sensor.

Alternatively, if the controller 160 detects both the global reference feature and the object feature in the second image but determines that the resolution of the object feature in the field of view of the optical sensor is below a threshold resolution (e.g., a dimension or area of the object feature shown in the second image is less than a threshold dimension or area sufficient to precisely locate the object reference frame), the controller 160 can: virtually locate the preplanned trajectory relative to the global reference feature; and continue to register motion of the end effector 140 to the global reference feature rather than the object feature. When the computer system detects the object feature of sufficient resolution in a subsequent image recorded by the camera 150 at a subsequent time, the computer system can transition to registering motion of the end effector 140 to the target object, such as by virtually aligning the object keypoint of the preplanned trajectory to the object feature.

Furthermore, once the controller 160 transitions to registering motion of the end effector 140 to the object feature, the controller 160 can continue to: detect the global reference feature in subsequent images recorded by the camera 150; and recalculate the position of the global reference frame relative to the robotic arm based on the position of the global reference feature in these subsequent images. The controller 160 can thus rapidly resort back to registering motion of the end effector 140 to the global reference feature if the controller 160 fails to detect the object feature in subsequent images. Over time, the controller 160 can additionally or alternatively implement check motion of the end effector 140 along the preplanned trajectory within the object reference frame against the preplanned trajectory defined in the global reference frame in order to detect and reject errors in either of the object reference frame or the global reference frame.

In one example, the global reference feature includes a predefined reference fiducial arranged on a fastener dispenser containing a set of threaded fasteners; and the controller 160 navigates the end effector 140 along a preplanned trajectory—defined relative to this predefined reference fiducial—toward the fastener dispenser. As the end effector 140 approaches the fastener dispenser and the target object—defining a fastener in a release position in the fastener dispenser—fills a sufficient area of the field of view of the camera 150, the controller 160 can: match a set of features extracted from images recorded by the camera 150 to a unique constellation of features representing a screw head to identify the target object in these images; and then register motion of the end effector 140 to this fastener until the fastener is no longer in the field of view of the camera 150 or until the end effector 140 engages the fastener at the end of the preplanned trajectory. (In this example, as the end effector 140 approaches the fastener, the controller 160 can also drive an actuator in the end effector 140 to rotate a screw driver head extending from the end effector 140 into alignment with a driver receiver on the screw head.)

10.2 Object Reference Frame to Machine Reference Frame

The controller 160 can implement similar methods and techniques to transition from registering motion to the object feature to tracking motion of the end effector 140 within machine coordinates. For example, as the end effector 140 approaches the target object, the object feature may move beyond the field of view of the camera 150 due to a physical offset between the end effector 140 (or the interface surface) and the camera 150; therefore, once the controller 160 detects absence of the global reference feature and absence of the object feature in an image recorded along the current preplanned trajectory defined in the object reference frame, the controller 160 can transition to driving the set of actuators to move the end effector 140 into contact with the target object based on outputs of the angular position sensors and a motion model of the arm recently calibrated to the object reference frame as the end effector 140 approached this pose, as described above. In particular, the controller 160 can project the remainder of the preplanned trajectory from the object reference frame into the machine reference frame and implement closed-loop controls to sweep the end effector 140 along this remainder of the preplanned trajectory based on outputs of the position sensors in the arm and the locally-calibrated motion model of the arm, thereby moving the end effector 140 into contact with the target object.

Once the end effector 140 has fully traversed the preplanned trajectory and/or once a torque or force sensor in the arm or end effector 140 indicates that the end effector 140 has made contact with an object, the controller 160 can trigger the end effector 140 to engage the target object, such as by actuating a gripper integrated into the end effector 140 to grip target object, thereby coupling the target object to the end effector 140. With the target object now (rigidly) coupled to the end effector 140, the position of the object feature in the field of view of the camera 150 is no longer relevant to the subsequent trajectory of the end effector 140 in real space. Therefore, the controller 160 can therefore register subsequent motion to other than the object feature.

In one implementation, once the end effector 140 engages the target object, the controller 160 detects absence of the global reference feature and absence of a target feature—representing a release position for the target object—in a subsequent image recorded by the camera 150. Given absence of the global reference feature and absence of the target feature in this image, the controller 160: loads a second preplanned trajectory containing keypoints defined in machine coordinates; and then implements closed-loop controls to retract the end effector 140 along this second preplanned trajectory based on the locally-calibrated motion model of the arm and outputs of the position sensors arranged in the arm.

10.3 Machine Reference Frame to Global Reference Frame

As the end effector 140 moves along the second preplanned trajectory—such as extending from the object keypoint at which the end effector 140 engaged the target object to a target keypoint approximating a release position for the target object—the controller 160 can continue to scan images output by the camera 150 for the global reference feature (or for an alternate global reference feature) and then transition back into registering motion of the end effector 140 to the global reference feature when this global reference feature is detected. For example, while driving the end effector 140 through keypoints of the second preplanned trajectory defined in the machine coordinate system, the controller 160 can: detect the global reference feature in an image recorded by the camera iso; and then redefine the global reference frame relative to this global reference feature, import the second preplanned trajectory into the global reference frame, and implement closed-loop controls to move the end effector 140 through keypoints of the second preplanned trajectory now defined in the global reference feature.

(The controller 160 can similarly transition from the machine reference frame to the object reference frame, as shown in FIG. 3.)

10.4 Global Reference Frame to Target Reference Frame

As the end effector 140 moves along the second preplanned trajectory, the controller 160 can additionally or alternatively scan images output by the camera 150 for a target feature representing a release position for (or other position at which to manipulate) the target object. For example, the controller 160 can implement methods and techniques described above to: detect the target feature in the field of view of the camera 150; define a target reference frame in real space relative to this target feature; project the remainder of the second preplanned trajectory into this target reference frame (e.g., by virtually aligning the target keypoint of the second preplanned trajectory to the target feature based on the position of the target feature in the camera 150 field of view); and implement closed-loop controls to move the end effector 140 through keypoints of the second preplanned trajectory in the target reference frame toward to the release position.

In this implementation, as the end effector 140 approaches the target feature, the controller 160 can also: regularly recalibrate the motion model of the arm, as described above; and transition back into the machine reference frame to complete a remainder of the second preplanned trajectory if the target feature moves out of the field of view of the camera 150.

10.5 Release Routine

Once the end effector 140 has fully traversed the second preplanned trajectory (i.e., reached the target keypoint) and/or once a torque or force sensor in the arm or end effector 140 indicates that the end effector 140 has made contact with an object, the controller 160 can trigger the end effector 140 to execute a release routine, such as by opening a gripper to release the target or by driving the target object defining a threaded fastener into a corresponding bore.

In the example described above in which the target object includes a threaded fastener collected by the end effector 140 at the object keypoint of the (first) preplanned trajectory, the controller 160 can: scan images output by the camera 150 for the target feature coinciding with a (smooth or threaded) bore at a release position while executing the second preplanned trajectory; regularly recalculate the feature reference frame as the end effector 140 approaches the target feature; and drive the actuators in the arm to move the target object—coupled to the end effector 140—into contact with the bore at the release position. In response to the target object entering the release position, such as when the end effector 140 reaches the terminus of the second preplanned trajectory and/or when an output of a torque or force sensor in the arm indicates that the end effector 140 has made contact with an object, the controller 160 can trigger an actuator in the end effector 140 to rotate in a forward direction while driving actuators in the arm to advance the end effector 140 forward in a direction parallel to an axis of the target object and at a rate proportional to a rotational speed of the end effector 140, thereby driving the threaded fastener into the bore. During this routine, the controller 160 can track a power draw, back EMF, or torque output of the actuator, and then stop the actuator and drive the actuator to retract the end effector 140 from the release position (e.g., parallel to the axis of the threaded fastener) when a power draw, back EMF, or torque output of the actuator exceeds a threshold torque.

The controller 160 can then repeat the foregoing processes to once again execute the preplanned trajectory, collect a second target object at the object keypoint, navigate the end effector 140 along the second preplanned trajectory, and then execute a release routine once the end effector 140 has entered the target keypoint, etc. Alternatively, the controller 160 can load a different set of preplanned trajectories, such as to collect and install a second threaded fastener of the same or different type in a different position near the target position.

11. Example Application: Assembly Line and Screw Driver

In one application, the system 100 is installed near an assembly line and is configured to interface with units of an assembly (i.e., "target objects") moving along a conveyor. In this application, the controller 160 executes the forgoing methods and techniques to register to an assembly unit moving along the assembly line rather than to a carrier or other secondary object or fiducial on the conveyor when preparing to interface with (e.g., grasp or install a part onto) the assembly unit, thereby enabling use of low-precision carriers to locate units of the assembly without sacrificing accuracy of an operation performed on this assembly unit with the system 100 by registering to an assembly unit represented in a sequence of images recorded by the camera 150 rather than by registering to a carrier constraining the part or to a secondary fiducial nearby. In another application, the system 100 is configured to engage a screw and to drive the screw into a part or assembly; the controller 160 thus implements the foregoing methods and techniques to register motion of the arm to a screw (or to the screw head, to a drive socket on the head of the screw) specifically based on the position of the screw shown in a sequence of images recorded by the camera 150 as the controller 160 drives the end effector 140 toward the screw, thereby enabling the system 100 to locate a screwdriver—extending from an end effector 140 on the end of the arm—into a drive socket of the screw despite the accuracy with which the screw is presented by a screw dispenser nearby, as described below.

In the foregoing example application, the controller 160 can dynamically register motion of the arm to a screw (or to a screw head or to a drive socket on the screw head) as the controller 160 drives a screwdriver on the end of the arm through a preplanned trajectory to engage the screw, such as during a screw selection cycle. For example, at the beginning of a screw selection cycle, the controller 160 can calculate (or "preplan") a trajectory of the arm that moves the end effector 140 from its current location to a predicted location (e.g., in machine or machine coordinates) of a screw for subsequent selection by the end effector 140, moves the arm to a first keypoint along the preplanned trajectory, and then triggers the camera 150 to record a first image. The controller 160 then scans the first image for a feature representative of the drive socket on the head of the screw. For example, the controller 160 can generate a feature constellation containing features extracted from a region of the image predicted to contain the screw, match this constellation of features to a predefined template fingerprint of a drive socket on a screw, and map a labeled drive socket feature in the predefined template fingerprint to the constellation of features in the first image to identify the drive socket in the image.

The controller 160 can then implement methods and techniques described above to transform the size and geometry of the screw in the first image into the position of the camera 150 on the arm and then into the location of the screwdriver—on the end effector 140 on the end of the arm—relative to the drive socket on the screw when the arm is in the first position. In particular, the controller 160 can calculate the position of the entrance pupil of the camera 150 relative to the drive socket and then calculate the position of the tip of the screwdriver relative to the drive socket based on a known transformation from the entrance pupil of the camera 150 to the screwdriver tip. The controller 160 can then calculate a target second pose of the end effector 140—along or near the preplanned trajectory—that moves the screwdriver nearer to the drive socket and into coaxial and rotational alignment with the screw. For example, the controller 160 can calculate the second pose of the end effector 140 that deviates from the preplanned trajectory by up to a threshold distance, such as up to twice the tolerance range for location of the screw by a screw dispenser. The controller 160 can then implement closed-loop controls (e.g., based on position data read from position sensors in the joints, calibrated as described above) to move the arm from the first position to the second position.

Once the arm reaches the second position, the camera 150 can record a second image; and the controller 160 can scan the second image for the screw, as described above. In particular, because the second position is nearer the screw than the first position, the second image may represent the screw at a greater resolution than the first image. The controller 160 can thus implement the foregoing methods and techniques to calculate a third position for the arm along or near the preplanned trajectory—based on the position of the screw represented in the second image—to bring the screwdriver into position to precisely engage the screw.

The controller 160 can repeat this process to refine the trajectory of the arm as the screwdriver approaches the screw. Specifically, the controller 160 can repeatedly trigger the camera 150 to record images as the arm moves the camera 150 and the screwdriver closer to the drive socket of the screw, and each subsequent image can capture the screw at a greater resolution than its preceding image; based on higher-resolution optical data of the screw that becomes available with each subsequent image, the controller 160 can recalculate a trajectory (or modify a preplanned trajectory) of the arm to move the screwdriver tip from its current position to a final position in which the screwdriver is coaxially aligned with and inserted into the drive socket of the screw. (Furthermore, the controller 160 can identify the angular orientation of the drive socket on the screw head and rotate the screwdriver to align with the angular orientation of the drive socket on the screw head, such as once the tip of the screwdriver is determined to be within five centimeters of the screw.)

In one implementation in which the camera 150 is arranged on the end of the arm with its field of view including the tip of the screwdriver, the controller 160 can repeat the foregoing methods and techniques to bring the tip of the screwdriver into contact with the drive socket of the screw; the controller 160 can then confirm such contact based on a change in the output of a force sensor integrated into a joint of the arm and/or optically by identifying the screwdriver tip and the screw head and confirming proximity of the screwdriver tip to the screw head in an image recorded by the camera 150. Alternatively, in an implementation in which the field of view of the camera 150 excludes the screwdriver tip, the controller 160 can repeat the foregoing methods and techniques to execute and refine the trajectory of the arm until the screw is no longer visible in an image recorded by the camera 150 and then execute a final revision of the trajectory based on outputs of position sensors integrated into joints of the arm rather than based on additional images received from the camera iso. The controller 160 can then confirm that the screwdriver tip has contacted the screw based on changes in the output of a force sensor integrated into the arm and/or based on conclusion of the trajectory.

Therefore, by registering motion of the arm to the screw (i.e., a target object) rather than to other static features, carriers, or secondary objects around the arm, the controller 160 can accurately and repeatably navigate the tip of the screwdriver into the drive socket of a screw dispensed by a relatively low precision screw presenter, such as a screw presenter designer for human operators rather than robotic systems.

Once the screw is engaged by the screwdriver, the system 100 can begin to execute a second predefined trajectory to move the screw from its perch on a screw dispenser to a target bore in a target part or assembly nearby. For example, the system 100 can execute the second predefined trajectory until a target part defining a target bore comes into view of the camera 150. Once the target part and/or target bore are identified in images output by the camera 150, the controller 160 can implement methods and techniques described above to revise the second predefined trajectory as the arm moves the screwdriver tip and the screw toward the target part and into the target bore, such as while the target object is static or while the target object is moving along a conveyor or assembly line.

12. Manual Setup

In one variation shown in FIG. 2, the system 100 executes a second method S200, including, during a setup period: unlocking joints in the robotic arm in Block S210; as a user manually moves the robotic arm in real space, recording a sequence of images through an optical sensor mounted to the arm and defining a field of view coincident an operating field of the robotic arm in Block S220; detecting an interaction pose at which an end effector 140 on the robotic arm engages a template object in Block S230; based on a trajectory of the end effector 140 proximal the interaction pose and changes in positions of features detected in the sequence of images, correlating a template feature detected in the sequence of images with the template object in Block S240; and defining the trajectory relative to the template feature in the field of view of the optical sensor based on positions of the template feature in the sequence of images in Block S250

Figure 5:
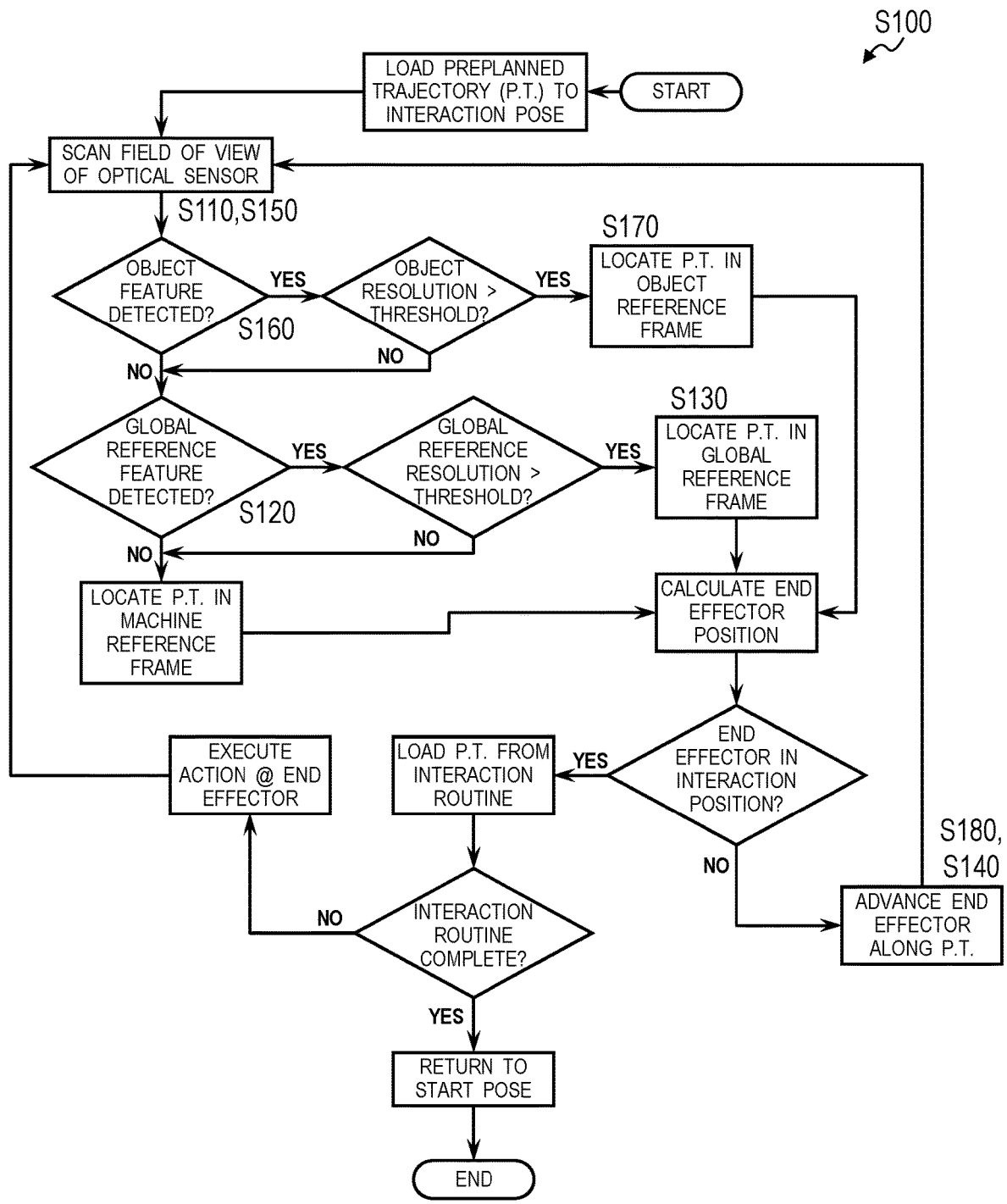
FIG. 5 is a flowchart representation of one variation of the first method.

During an operating period shown in FIG. 5, the system 100 can then: detect a first feature analogous to the template feature in the field of view of the optical sensor in Block S160; and autonomously replicate the trajectory at the robotic arm by driving a set of actuators within the robotic arm based on positions of the first feature in the field of view of the optical sensor in Block S180, as described above.

Generally, in this variation, the system 100 can define a preplanned trajectory located relative to a feature or constellation of features representative of a template object in the field near the robotic arm based on a path traversed by the end effector 140 while manually manipulated by a user. The system 100 can then autonomously replicate this preplanned trajectory according to methods described above.

12.1 Keypoints

Block S210 of the second method S200 recites unlocking joints in the robotic arm; and Block S220 of the second method S200 recites, as a user manually moves the robotic arm in real space, recording a sequence of images through an optical sensor mounted to the arm and defining a field of view coincident an operating field of the robotic arm. Generally, in Block S210, the system 100 transitions into an unlocked state in which actuators in the robotic system support the weight of the robotic system and the end effector 140 but also (actively) yield to torques input by the user into joints of the arm, thereby enabling the user to manually move the end effector 140 along a path in real space with minimal resistance. In Block S220, the system 100 collects data pertinent to reconstructing this path relative to a target object, such as both angular joint position data in machine coordinates through position sensors arranged in joints in the arm and images from an optical sensor arranged on a distal end of the arm proximal the end effector 140.

In one implementation, the operator places a template within an operating field of the robotic arm, such as on a fixture or a surface—near the robotic arm—on which units of similar objects will be arranged during future autonomous operating periods of the system 100. The operator then initializes a setup period at the system 100 (e.g., through a user interface executing on a computing device connected to the system 100), grasps the arm, manually draws the arm through a toolpath, and manually triggers various keypoints, such as: a start keypoint indicating the beginning of the path; an interaction keypoint indicating a position at which the end effector 140 engages a template object; and a completion keypoint indicating conclusion of the path, such as shown in FIG. 2.

In this implementation, the system 100 can read and store a position value from each joint in the arm and trigger the camera 150 to record a keypoint image at each keypoint entered by the operator. For example, in Block S220, the system 100 can: record an image at each keypoint in a sequence of keypoints along a path traversed by the end effector 140 during the setup period; and record a sequence of joint postures of joints in the robotic arm in machine coordinates at each keypoint in the sequence of keypoints. In Block S250 described below, the system 100 can then: define the trajectory of the end effector 140 relative to a template feature detected in these images based on positions of the template feature in these images and a known offset between the optical sensor and the end effector 140; and also define a sequence of target joint postures of joints in the robotic arm along the trajectory based on the sequence of joint postures. When autonomously replaying the trajectory in Blocks S160 and S180, the system 100 can: drive the set of actuators in the arm to approximate the sequence of target joint postures; but also deviate from these target joint postures based on positions of an object feature—analogous to the template feature—detected in the field of view of the optical sensor in order to move the end effector 140 along the trajectory relative to this object feature. The system 100 can therefore register motion of the end effector 140 to the object feature while also mimicking—as much as possible—the original motion of each joint of the arm recorded during the setup period.

Alternatively, the system 100 can collect a sequence of images in Block S220 and define a repeatable trajectory based (exclusively) on optical data extracted from these images, such as positions of the template feature, a global reference feature, etc. However, the system 100 can collect any other data of any other type in Block S220.

12.2 Interaction Position

Block S230 of the second method S200 recites detecting an interaction pose at which an end effector 140 on the robotic arm engages a template object in a field proximal the robotic arm. Generally, in Block S230, the system 100 identifies a particular pose at which the end effector 140 engages (e.g., contacts or modifies) the template object, such as in the form of a position of the template feature (or the global reference feature or other feature) in the field of view of the optical sensor and/or in the form of a combination of angular positions of joints in the robotic arm.

In one implementation, the system 100 detects the interaction pose in response to selection of a manual trigger by the user. For example, the system 100 can include a physical button arranged on the robotic arm, on the base, or on a handheld controller 160 connected to the robotic arm. Alternatively, the system 100 can interface with a graphical user interface including a virtual button selectable by the user. The system 100 can register selection of the real or virtual button as an indicator that the robotic arm is occupying the interaction pose. (The system 100 can register selection of the real or virtual button as a keypoint, as described above.)

In this implementation, the system 100 can also initiate an action at the end effector 140 and/or at other actuators in the arm in response to selection of the button. For example, the user can select an interaction routine or action from a menu in the graphical user interface, such as: closing a gripper integrated into the end effector 140 from an open to a closed position; rotation of a screwdriver integrated into the end effector 140 until a threshold drive torque is reached; or actuating of a welding tip integrated into the end effector 140 at a target current value and target shield gas flow rate; etc. The user can link this interaction routine to manual selection of the button, and the system 100 can: record the interaction pose in Block S230; and trigger the end effector 140 to execute this interaction routine. The system 100 can also: write a prompt to the trajectory to execute this same interaction routine when the end effector 140 occupies this same interaction pose during a subsequent operating period in Block S250; and then autonomously execute the interaction routine in response to the robotic arm arriving at the interaction pose—defined relative to a first feature in the field of view of the optical sensor analogous to the template feature—during this subsequent operating period in Block S180. Following selection of the manual trigger to initiate the interaction routine, the system 100 can: continue to record images and/or angular positions of joints in the robotic arm in Block S220; record a second selection of the manual trigger; deactivate the interaction routine in response to selection of the manual trigger; define a release pose in response to selection of the manual trigger; and write the trajectory from the interaction pose to the release pose—relative to the template feature—in Block S250. (The system 100 can alternatively define: an approach trajectory leading up to the interaction pose; and a distinct interaction trajectory between the interaction pose and the release pose, as described below.)

In another implementation, the end effector 140 can include a force sensor, impact sensor, contact sensor, proximity sensor, or a sensor of any other type configured to output a signal indicating that the end effector 140 is immediately adjacent or has contacted the template object. The system 100 can thus record an interaction pose of the end effector 140 in response to detecting a change in the output of this sensor in Block S230. The system 100 can also automatically execute an interaction routine—preselected by the operator—at this interaction pose, such as described above.

In yet another implementation, the system 100 can: record a sequence of joint postures of joints in the robotic arm—such as in the machine reference frame—during the setup period; detect a directional reversal of the end effector 140 in real space in the sequence of joint postures; and record the interaction pose at this directional reversal. For example, the system 100 can: identify a sequence of advancing into a position, pausing for a period of time, and then retracting from this position—in the sequence of joint postures—as a directional reversal of the end effector 140; identify a particular image recorded by the optical sensor during the pause period; identify the position of the template feature (or the global reference feature, etc.) in the particular image; and then define the interaction pose of the end effector 140 based on this position of the template feature in the particular image in Block S230. Therefore, in this implementation, the system 100 can: automatically characterize the interaction pose as corresponding to a severe change (e.g., an inflection) in the path of the end effector 140; and then define the interaction pose relative to the template feature based on a position of the template feature in a particular image, in the sequence of images, recorded nearest a time of this severe change in the path of the end effector 140.

However, the system 100 can implement any other method or technique to identify the interaction pose in Block S230.

12.3 Template Feature

Block S240 of the second method S200 recites, based on a trajectory of the end effector 140 proximal the interaction pose and changes in positions of features detected in the sequence of images, correlating a template feature detected in the sequence of images with the template object. Generally, in Block S240, the system 100 identifies a particular feature—from many features detected in images recorded by the optical sensor during the setup routine—that represents the target object analogous to other objects that the end effector 140 is designated to contact or modify during subsequent repetitions of the trajectory in Block S180. For example, in Block S240, the system 100 can identify a singular feature or a constellation of features that represent: an interaction surface on the template object, such as a bore into which the system 100 inserts a fastener or two opposing surfaces that the end effector 140 grips when lifting the template object; a surface on the template object but offset from the interaction surface, such as an edge or vertex adjacent the interaction surface but that remains in the field of view of the optical sensor when the end effector 140 occupies the interaction pose; or a surface on a jig, fixture, or other equipment known to reliably locate units of target objects analogous to the template object.

In one implementation, the system 100 records joint poses of the robotic arm as the operator moves the robotic arm through space, such as at each automatically-defined or at manually-indicated keypoint wherein a set of angular positions of each joint of the arm is recorded in machine coordinates at each keypoint, as described above. The system 100 can then: transform each pose into a pose of the end effector 140 (e.g., the interface surface on the end effector 140) in real space based on a known length of each segment of the robotic arm; interpolate between these end effector 140 poses—leading up to the interaction position—into a trajectory of the end effector 140 defined in the machine reference frame; and then project these trajectory into one or more images recorded by the optical sensor during the setup routine based on a known position of the optical sensor on the robotic arm (e.g., relative to the interface surface on the end effector 140) and various properties of the optical sensor. For each of these images for which the end of the trajectory falls within the image, the system 100 can identify an object in the image that coincides with the end of the trajectory; extract features from regions of these images corresponding to the end of the trajectory; confirm that this object represents the template object based on similarities between features extracted from these images; and then store a single matched feature or a constellation of such matched features as the template feature. (The system 100 can also confirm that the selected feature represents the template object based on whether this feature (or constellation of features) increases in scale in the sequence of images as the robotic arm approaches the interaction pose.)

Therefore, in this implementation, the system 100 can: calculate a trajectory of the end effector 140 as the end effector 140 approaches the interaction pose; project this trajectory onto an image recorded by the optical sensor during the setup routine; extract a feature coincident the end of this trajectory in this image; and store this feature as the template feature in Block S240.

In a similar implementation, the system 100 can identify the template object based on optical data extracted from the start, interaction, and final images collected during the setup period. For example, the system 100 can: project the interaction image onto an existing three-dimensional sparse map of the system's environment; and then project a known position of an interface surface on the end effector 140 relative to the camera's entrance pupil onto the projected interaction image to define an interaction point, line, or area in the three-dimensional sparse map at which the interface surface engages the template object. The system 100 can project the initial image onto the three-dimensional sparse map of the system's environment and implement computer vision techniques, such as object detection or edge detection, to identify the template object or a specific feature on the template object—in the initial, pre-interaction image—intersected by the interaction point, line, or area in the three-dimensional sparse map. Similarly, the system 100 can project the final image onto the three-dimensional sparse map of the system's environment and implement computer vision techniques to identify the template object or the specific feature on the template object—in the post-interaction image—intersected by the interaction point, line, or area in the three-dimensional sparse map. Specifically, the system 100 can: fuse a known offset between the end effector 140 and the camera 150 and the interaction image to determine a point, line, or area in real space at which the end effector 140 engages a template object; map this point, line, or area onto the initial image to identify the template object or a feature of the interaction image in a pre-interaction state; and map this point, line, or area onto the final image to identify the template object or feature in a post-interaction state.

In another implementation, the system 100 can: receive a virtual model of the template object; transform this virtual model into a template feature or constellation of template features; scan images recorded by the optical sensor during the setup routine for the template feature or constellation of template features; and identify the template object in these images based on sufficient alignment between features extracted from these images and the template feature or constellation of template features, such as described below.

However, the system 100 can implement any other method or technique to automatically detect the template feature or the template object in the field of view of the optical sensor in real-time or asynchronously (e.g., in images recorded by the optical sensor during the setup routine).

12.4 Preplanned Trajectory

Block S250 of the second method S200 recites defining the trajectory relative to the template feature in the field of view of the optical sensor based on positions of the template feature in the sequence of images. Generally, in Block S250, the system 100 can define a preplanned trajectory for the end effector 140 relative to the template feature (e.g., target angular positions of joints in the arm) based on data collected during the setup routine in which the user manually moves the robotic arm through real space, as shown in FIG. 2.

In one implementation, the system 100: locates a template object reference frame on the template feature detected in each image; calculates a pose of the end effector 140 in the template object reference frame in each image based on a known offset between the end effector 140 and the optical sensor and based on the position, scale, skew, and/or orientation, etc. of the template feature in the image; and aggregates these poses into a preplanned trajectory.

Similarly, the system 100 can: detect a constellation of template features—representing the template object—present and increasing in scale in a subset of the sequence of images as the robotic arm approaches the interaction pose in Block S240; and then define the preplanned trajectory—including position and orientation of the end effector 140 at multiple points along a path in real space—relative to the constellation of template features in the field of view of the optical sensor based on positions of the constellation of template features in the subset of images in Block S250. As described above, the system 100 can then: scan the field of view of the optical sensor for a first constellation of features analogous to the constellation of template features in Block S160; and then drive the set of actuators within the robotic arm—based on positions and orientations of the first constellation of features in the field of view of the optical sensor—to move the end effector 140 along the preplanned trajectory and into the interaction pose in Block S180.

However, the system 100 can implement any other methods or techniques to define the preplanned trajectory in Block S250, such as described above.

12.5 Segmented Trajectory

In this variation, the system 100 can also define multiple segments of the preplanned trajectory, as shown in FIG. 5.

In one implementation, the system 100 generates: a first trajectory segment defined relative to the template feature and applicable while the template feature remains in the field of view of the optical sensor; and a second trajectory segment defined relative to a second feature and applicable once the template feature moves outside the field of view of the optical sensor, such as if proximity of the end effector 140 to the template object obscures the template feature from the field of view of the camera 150. For example, in Block S250, the system 100 can: detect the template feature in a first image in the sequence of images recorded during the setup period; determine that the template feature is absent in a second image, in the sequence of images, recorded after the first image and before the end effector 140 enters the interaction pose; detect a second template feature present in the first image and in the second image, such as coincident or adjacent the template object; defining a first segment of the trajectory—preceding the interaction pose—relative to the template feature; and define a second segment of the trajectory—succeeding the first segment of the trajectory and containing the interaction pose—relative to the second template feature. During a subsequent operating period, the system 100 can then drive the set of actuators in the robotic arm to replicate the first segment of the trajectory based on positions of a first feature—analogous to the template feature—detected in the field of view of the optical sensor. Furthermore, in response to completing the first segment of the trajectory, the system 100 can drive the set of actuators to replicate the second segment of the trajectory based on positions of a second feature—analogous to the second template feature—detected in the field of view of the optical sensor.

For example, in Block S250, the system 100 can define a first segment of the trajectory relative to the template feature that represents an interaction surface on the template object, such as a target bore into which the end effector 140 is to insert a reamer, a target bore into which the end effector 140 is to insert a fastener, or a target surface that the end effector 140 is to grip, etc.). The system 100 can also define a second segment of the trajectory relative to a second template feature that represents an edge of the template object and is offset from the interaction surface on the template object, such as a second bore on the template object, a perimeter of the template object, or a boss on the template object offset from the target bore but remaining in the field of view of the optical sensor as the end effector 140 enters the interaction pose. During a subsequent operating period, the system 100 can: detect a first feature that is analogous to the template feature and detect a second feature analogous to the second template feature in the field of view of the optical sensor in Block S160, wherein the first feature and the second feature both represent a target object analogous to the template object; and drive actuators in the arm to move the end effector 140 along the first trajectory segment while the first feature remains in the field of view of the optical sensor in Block S180. Once the first feature falls outside of the field of view of the optical sensor or is obscured from the optical sensor, the system 100 can drive the actuators to move the end effector 140 along the second trajectory segment, such as to locate the second template feature in a position in the field of view of the optical sensor associated with the interaction pose in Block S180, wherein the interface surface on the end effector 140 contacts a region of the target object represented by the first feature when the end effector 140 occupies the interaction pose.

Therefore, in this implementation, the system 100 can calculate multiple trajectory segments in Block S250, wherein each trajectory segment is defined relative to a different feature (or constellation of features) that remains in the field of view of the optical sensor as the end effector 140 traverses this trajectory segment; and the system 100 can then replicate these trajectory segments autonomously based on positions of analogous features detected in the field of view of the optical sensor during subsequent operating periods.

In a similar implementation, the system 100 can segment the trajectory based on resolutions of various features in the sequence of images recorded by the optical sensor during the setup period. For example, the system 100 can: detect a first template feature (representing the template object) at a resolution less than a threshold resolution in a first subset of images in the sequence of images; detect a global reference feature—proximal the first template feature and distinct from the target object—at a resolution greater than the threshold resolution; and detect the first template feature at a resolution greater than the threshold resolution in a second subset of images succeeding the first subset images in the sequence of images in Block S230. The system 100 can then: define a first segment of the trajectory relative to the global reference feature based on positions of the global reference feature in the first subset of images; and define a second segment of the trajectory—succeeding the first segment of the trajectory and containing the interaction pose—relative to the first template feature based on positions of the first template feature in the second subset of images in Block S250. During a subsequent operating period, the system 100 can: drive the actuators in the robotic arm to replicate the first segment of the trajectory based on positions of a second feature—analogous to the global reference feature—detected in the field of view of the optical sensor; and then, in response to completing the first segment of the trajectory, drive the actuators to replicate the second segment of the trajectory based on positions of a first feature—analogous to the first template feature—detected in the field of view of the optical sensor in Block S180.

In yet another implementation, the system 100 can segment the trajectory into: an approach trajectory defining the end effector's approach to the interaction pose; and an interaction trajectory defining a path traversed by the end effector 140 from the interaction pose to a release pose over which the end effector 140 engages the template object. For example, the system 100 can respond to receipt of a manual trigger by storing the pose of the robotic arm (e.g., relative to the template feature) at this time as an interaction pose, executing an interaction routine, and storing a release pose of the robotic arm at the conclusion of the interaction routine, as described above. The system 100 can also: define a first segment of the trajectory that precedes the interaction position and is located relative to the template feature, such as based on positions of the template feature in images recorded by the optical sensor prior to selection of the manual trigger at the interaction pose; and also define a second segment of the trajectory that succeeds the interaction position (e.g., that extends from the interaction pose to the release pose) and is located relative to a second feature (e.g., a second feature on the template object or the global reference feature, etc.) based on positions of the second feature in images, in the sequence of images, recorded after selection of the manual trigger. In this example, the system 100 can thus record the path of the end effector 140—relative to an optical feature near the robotic arm—as the end effector 140 interacts with the template object, such as to insert a threaded fastener into a bore in the template object, to lay a weld bead along the template object, or to grasp and retract the template object, etc., and then define a second segment of the trajectory, including a state of an actuator in the end effector 140, based on this path in Block S250. The system 100 can also write a prompt to execute the interaction routine upon arrival at the interaction pose to the second segment of the trajectory in Block S250. During a subsequent operating period, the system 100 can: autonomously drive the set of actuators to replicate the first segment of the trajectory based on positions of a first feature—analogous to the first template feature—in the field of view of the optical sensor over a first period of time; and then autonomously drive the set of actuators in the arm to replicate the second segment of the trajectory based on positions of the secondary feature—analogous to the second template feature—in the field of view of the optical sensor during execution of the interaction routine over a second period of time succeeding the first period of time. Furthermore, in this example, when executing the second segment of the trajectory in Block S180, the system 100 can: autonomously execute the interaction routine—along the second segment of the trajectory—in response to the robotic arm arriving at the interaction pose, such as defined relative to the first and/or second feature in the field of view of the optical sensor.

However, the system 100 can define any other number of segments of the trajectory relative to any other feature detected in images recorded by the optical sensor during the setup period and based on any other parameters or schema in Block S250. The system 100 can also autonomously replicate this preplanned trajectory during an operating period in Block S180, as described above.

12.6 Context+Interaction Checks

As shown in FIG. 2, the system 100 can also record a pre-interaction image prior to the robotic arm occupying the interaction pose and record a post-interaction image once the robotic arm leaves the interaction pose during the setup period in Block S220. In this variation, the system 100 can further execute: Block S260 of the second method S200, which recites, during the setup period, detecting a first difference between the pre-interaction image and the post-interaction image proximal the template feature; and Block S262, which recites, during the operating period, recording a first image prior to the robotic arm approximating the interaction pose relative to the first feature, recording a second image once the robotic arm leaves the interaction pose, and confirming completion of the trajectory in response to a second difference between the first image and the second image proximal the first feature approximating the first difference.

Generally, in this variation, the system 100 can determine "intent" of the trajectory based on differences—occurring proximal the template object—between images recorded during the setup period, such as before and after the end effector 140 occupies the interaction pose. The system 100 can then determine that the end effector 140 has properly realized this intent with another target object during a subsequent operating period based on similar differences—occurring proximal the target object—between images recorded during the operating period. For example, the system 100 can: align a pre-interaction image recorded prior to the end effector 140 entering the interaction pose (or recorded once the end effector 140 enters the interaction pose) to a pose-interaction image recorded once the end effector 140 leaves the interaction pose (or recorded once the end effector 140 reaches the release pose upon completion of the interaction routine); subtract the pre-interaction image from the post-interaction image or otherwise calculate a difference between the pre- and post-interaction images proximal the template object detected in the images; and store this difference, which may represent installation of a screw, assembly of a second part onto the target object, or removal of material (e.g., drilling a hole) in the target object.

The system 100 can thus identify and store a change to the state of the target object that occurred during the setup period.

In Block S250, the system 100 can thus generate a preplanned trajectory: defined relative to optical features predicted to fall in the field of view of the camera 150 during a subsequent operating period; including an interaction routine; and associated with an "intent" of the trajectory (e.g., a change to the target object resulting from execution of the trajectory). The system 100 can automatically replay this trajectory and interaction routine to interact with a target object—analogous to the template object—during a subsequent operating period, as described above. To confirm that the system 100 achieved its designated intent with respect to the target object, the system 100 can: implement repeat methods described above to: align a pre-interaction image recorded prior to the end effector 140 entering the interaction pose (or recorded once the end effector 140 enters the interaction pose) to a pose-interaction image recorded once the end effector 140 leaves the interaction pose (or recorded once the end effector 140 reaches the release pose upon completion of the interaction routine); subtract the pre-interaction image from the post-interaction image or otherwise calculate a difference between the pre- and post-interaction images proximal the template object detected in the images; and confirm that the system 100 achieved its intent if this difference detected during the operating period sufficiently matches the difference detected during the setup period. However, if these differences fail to align sufficiently, the system 100 can repeat the trajectory, repeat the interaction routine, or flag the target object for manual inspection or correction, etc.

However, the system 100 can implement any other methods or techniques to identify the intent of the trajectory based on data collected during the setup period and to confirm that this intent was achieved by the system 100 during a subsequent operating period.

13. Virtual Model

Figure 6:
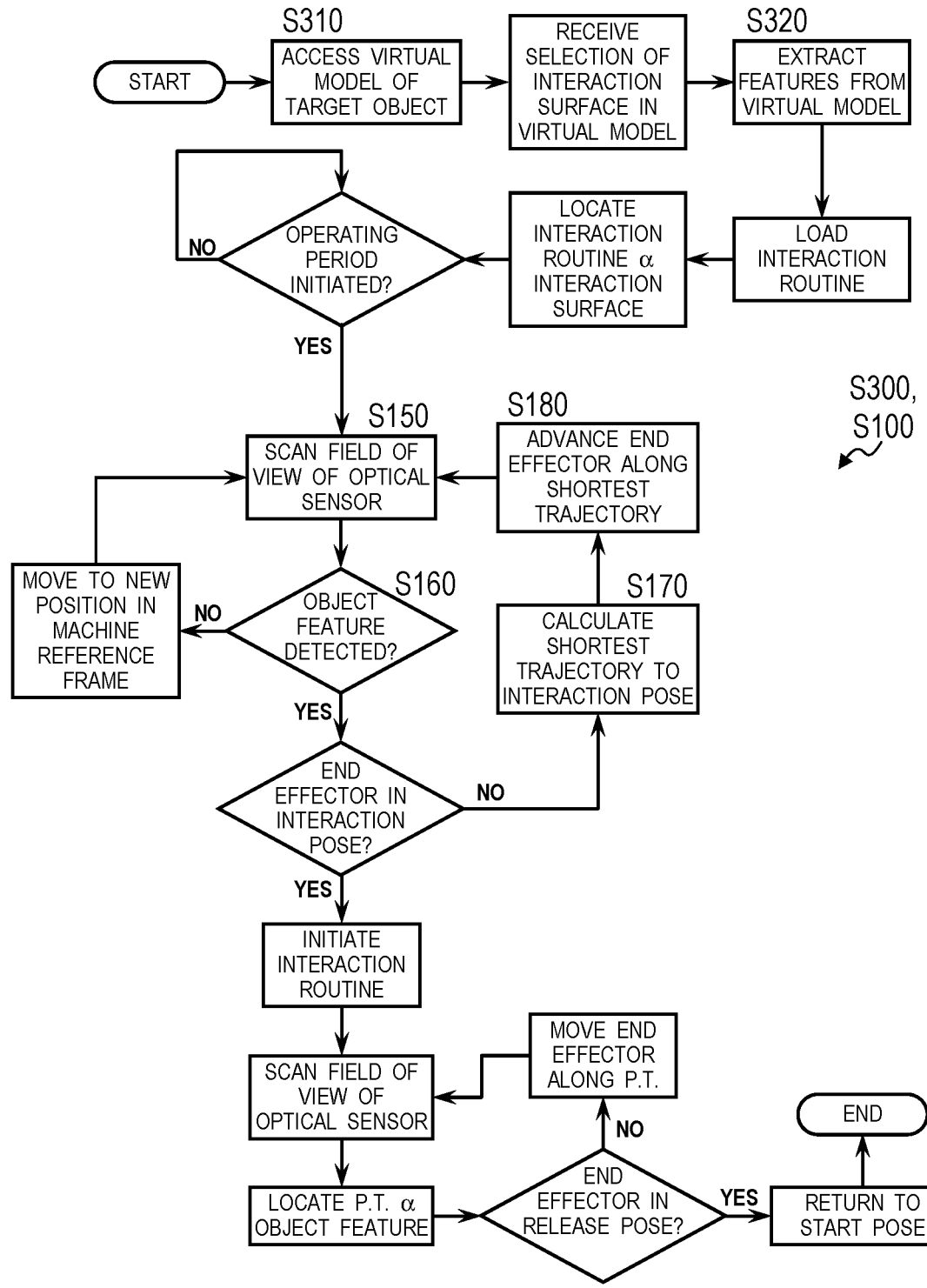
FIG. 6 is a flowchart representation of a third method and one variation of the first method.

In one variation shown in FIG. 6, the system 100 executes a third method S300, including: accessing a virtual model of the target object in Block S310; extracting an object feature representing the target object from the virtual model in Block S320. The system 100 can then, at the robotic arm: scan a field of view of an optical sensor for the object feature, the optical sensor arranged on a distal end of the robotic arm proximal an end effector 140 in Block S160; in response to detecting the object feature in the field of view of the optical sensor, calculate a physical offset between the target object and the end effector 140 based on a position of the object feature in the field of view of the optical sensor and a known offset between the optical sensor and the end effector 140 in Block S110; and drive a set of actuators in the robotic arm to reduce the physical offset in Block S180.

Generally, in this variation, the system 100 can extract an object feature or constellation of object features representing a target object from an existing virtual model (e.g., a computer-aided drafting or "CAD" model) of the target object in Blocks S310 and S320; scan the field of view of the optical sensor on the robotic arm for this object feature or constellation of object features; identify a target object when a sufficient match to this object feature is detected in Block S160; and then calculate—in real-time—an ad-hoc trajectory that, when executed by actuators in the robotic arm, drives the end effector 140 toward the target object in Block S110. The system 100 can then drive the actuators in the robotic arm according to this trajectory in Block S180 and regularly repeat this process to refine the ad hoc trajectory as the end effector 140 approaches the target object. In particular, rather than autonomously replicate a preplanned trajectory defined relative to the object feature and generated based on a path traversed by the end effector 140 during a manual setup period, the system 100 can access existing data (e.g., a CAD model) representative of the target object and automatically navigate toward the target object in real space based on positions of features—matched to these existing data—detected in the field of view of the optical sensor on the robotic arm, thereby avoiding a need for a user to manually manipulate the robotic arm or otherwise manually define a preplanned trajectory prior to the system 100 interacting with the target object.

13.1 Model to Object Features

Block S310 of the third method S300 recites accessing a virtual model of the target object; and Block S320 of the third method S300 recites extracting an object feature representing the target object from the virtual model. Generally, in Blocks S310 and S320, the system 100 accesses optical data that the system 100 can later apply to identify a corresponding target object in real space and to autonomously navigate the end effector 140 to this target object.

In one implementation, the system 100 (or an external computer system or software program in communication with the system 100) receives a CAD model selected by the user, such as uploaded to the system 100 via a graphical user interface or other portal hosted by the system 100, in Block S310. The system 100 can then extract a three-dimensional constellation of features representing the target object from the virtual model in Block S320. For example, the system 100 can transform the CAD model into a virtual point cloud, transform clusters of points into edge and vertex features around multiple faces of the virtual model, and then extract a unique set of edge features and vertex features from multiple sides of the virtual model in Block S320, thereby forming a constellation of features that represent the target object in many possible orientations relative to the optical sensor on the robotic arm. In Block S160, the system 100 can then scan an image—recorded by the optical sensor— for a cluster of features defining relative sizes, geometries, and positions approximating a subset of this set of edge features and vertex features, such as described above.

During a subsequent operating period, the system 100 can: record a first image through the optical sensor; extract a set of features from the first image; and match a subset of these features to a subset of the three-dimensional constellation of features (i.e., a subset of the constellation of features that would be visible to the optical sensor given the current relative positions of the optical sensor and the target object) in order to identify the target object in the field of view of the optical sensor in Block S160. The system 100 can then: calculate a linear offset and a rotational offset from the end effector 140 to the target object based on a position and an orientation of the subset of features in the first image in Block S110; and then drive actuators in multiple joints in the robotic arm to reduce this linear offset and rotational offset between the end effector 140 and the target object in Block S180, as described above.

13.2 Feature Extraction

In Block S320, the system 100 can extract—from the virtual model—features representing an interaction surface on the target object (i.e., a surface or physical feature on the target object that the end effector 140 is to contact or otherwise interface with). For example, the system 100 can receive an indicator of an interaction surface on the virtual model, such as selection of the interaction surface on the virtual model by the user when viewing the virtual model with the graphical user interface. The system 100 can then extract from the virtual model a particular object feature or constellation of object features representing this interaction surface. (Similarly, the system 100 can extract from the virtual model a constellation of object features from multiple faces of the virtual model, wherein features representing the interaction surface are assigned greatest weight.) The system 100 can then: identify the interaction surface near the robotic arm in Block S160 based on presence of a set of features in the field of view of the optical sensor that sufficiently match this constellation of features; calculate a physical offset between the interaction surface and an interface surface on the end effector 140 in Block S110 based on the position and orientation of the set of features in the field of view of the optical sensor and a known offset between the optical sensor and the interface surface on the end effector 140; and then drive the set of actuators to move the interface surface on the end effector 140 into contact with the interaction surface on the target object based on this physical offset.

In a similar implementation, the system 100 can access a pre-action virtual model of the target object and a post-action virtual model of the target object in Block S320; detect a difference between the pre-action virtual model of the target object and the post-action virtual model of the target object; and then extract the object feature from a region of the pre-action virtual model of the target object coinciding with this difference in Block S320. For example, the system 100 can access the pre-action virtual model that represents a first target object defining a threaded fastener and the post-action virtual model that represents a virtual assembly of the first virtual model installed on a second virtual model of a second target object. In this example, system 100 can determine that the first target object is a threaded fastener specified for installation into the threaded bore of the second target object based on the virtual assembly and virtual geometries of the target objects represented in their corresponding virtual models. The system 100 can then extract, from the pre-action virtual module of the threaded fastener, a target feature or constellation of target features that represent the head of the threaded fastener. In this example, the system 100 can also select an interaction routine that defines a preplanned trajectory for engaging the head of the threaded fastener with a screwdriver on the end effector 140 and locate this preplanned trajectory according to the target feature or constellation of target features. During a subsequent operating period, the system 100 can; scan the field of view of the optical sensor for the target feature or constellation of target features representing the head of the threaded fastener in Block S160; autonomously navigate the end effector 140 to a pose that coaxially aligns the screwdriver with the threaded fastener and inserts the screwdriver into the head of the threaded fastener based on position by locating the preplanned trajectory on the target feature or constellation of target features in the field of view of the optical sensor in Block S180. The system 100 can implement similar methods and techniques: to extract a second object feature or constellation of object features representing a threaded bore in a second target object from a second virtual model of the second target object in Block S320; to detect the second object feature or constellation of object features in the field of view of the optical sensor in Block S160 once the end effector 140 has engaged the threaded fastener; to move the end effector 140—with the threaded fastener—into position over the threaded bore on the second target object; to align the screwdriver to the threaded bore; and to insert the threaded fastener into the threaded bore in Block S180, such as by executing a preplanned trajectory in a predefined interaction routine for inserting a threaded fastener into a threaded bore, as described below. (In this implementation, the system 100 can also assign greater weight to such features representing the interaction surface on the target object, such as described above.)

13.3 Preplanned Trajectories and Interaction Routines

As shown in FIG. 6, the system 100 can also access and locate a preplanned trajectory—such as representing an interaction routine—relative to the constellation of features representing the target object (or the interaction surface on the target object specifically) extracted from the virtual model. For example, the system 100 can automatically select an interaction routine—from a predefined set of interaction routines—based on a type or other characteristic of the object feature selected from the virtual model. Alternatively, the user can manually select the interaction surface on the virtual model and insert an interaction routine—selected from the predefined set of interaction routines—onto this interaction surface in the virtual model through the graphical user interface. The selected interaction routine can define an interaction pose, a release pose, a preplanned trajectory between the interaction and release poses, and an action executable by the end effector 140 while traversing this path; and the system 100 can locate the preplanned trajectory relative to the constellation of template features representing the target object generally or representing the interaction surface more specifically in the virtual model.

In this implementation, the preplanned trajectory can also define: an approach direction, an approach speed, and an approach orientation of the end effector 140 between the interaction pose and the release pose, such as relative to a template feature; and an action executable by the end effector 140 during the preplanned trajectory, such as starting at the interaction pose and ceasing at the release pose. The system 100 can also interface with the user through the graphical user interface to set various parameters of the preplanned trajectory. Once the target object is detected in the field of view of the optical sensor in Block S160, the system 100 can navigate the end effector 140 to the interaction pose. For example, the system 100 can calculate a shortest viable trajectory from its current pose to the interaction pose thus located relative to the object feature detected in the field of view of the optical sensor; drive the set of actuators to move the end effector 140 from its current pose to the interaction pose along this shortest viable trajectory; and implement closed-loop controls, as described above, to regularly recalculate this shortest viable trajectory until the end effector 140 has reached the interaction pose in Block S180. The system 100 can then implement similar methods to drive the end effector 140 along the preplanned trajectory toward the release pose while the end effector 140 executes the action defined in the interaction routine and then retract the end effector 140 from the target object once the end effector 140 reaches the release pose.

In one example in which the interaction routine defines a threaded fastener insertion cycle, such as described above, the system 100 can: coaxially align a screwdriver on the end effector 140 to a threaded bore in the target object with the tip of the screwdriver linearly offset ahead of the bore by a distance slightly greater than a specified length of the fastener to be inserted in the target object (such as for a fastener length and thread specified by the user in the graphical user interface); coaxially align the screwdriver to the threaded bore in the target object with the tip of the screwdriver approximately flush with the adjacent surface of the target object (such as for a countersunk fastener specified by the user through the graphical user interface); and the system 100 can cease rotation of the screwdriver and retract the end effector 140 from the target object when a torque on the screwdriver exceeds a threshold torque (such as specified by the user in the graphical user interface) when the tip of the screwdriver is within a threshold distance from the adjacent surface of the target object.

Therefore, in this implementation, the system 100 can: retrieve a preplanned trajectory of an interaction routine, wherein the preplanned trajectory is defined relative to a template feature in Block S310; scan the field of view of the optical sensor for an object feature—analogous to a template feature—in Block S160; virtually align the template feature to the object feature detected in the field of view of the optical sensor to locate the preplanned trajectory relative to the object feature in Block 170, wherein the preplanned trajectory extends from an interaction pose to a release pose offset from and succeeding the interaction pose, and wherein the end effector 140 contacts the target object between the interaction pose and the release pose; drive the set of actuators to move the end effector 140 from its current pose to the interaction pose in Block S180; and then, in response to entering the interaction pose, drive the set of actuators to move the end effector 140 from the interaction pose to the release pose along the preplanned trajectory—located relative to the object feature in the field of view of the optical sensor—when the end effector 140 executes an action specified in the interaction routine.

In yet another implementation, the system 100 can implement similar methods and techniques to load a second virtual model of a second target object, extract features representative of the second target object, and to detect the second target object in the field of view of the optical sensor during an operating period in which the system 100 also interacts with the (first) target object. The system 100 can also link an interaction routine from the first target object to the second target object, such as in real-time based on detected positions of features corresponding to these target objects in the field of view of the optical sensor.

For example, during an operating period, the system 100 can: locate a first preplanned trajectory to grasp a first target object relative to a feature representing this first target object and execute this first preplanned trajectory; and locate a second preplanned trajectory to align the first target object to a second target object relative to a feature representing this second target object and execute this second preplanned trajectory to place or insert the first target object on or into the second target object.

In the foregoing example, the system 100 can access a second virtual model of a second target object in Block S310 and extract a second object feature representing the second target object from the second virtual model in Block S320, such as described above. During the operating period the system 100 can execute the first preplanned trajectory— once the end effector 140 reaches the interaction pose, as described above—by driving the set of actuators to move the end effector 140 into contact with the target object at the release pose and then triggering the end effector 140 to grasp the target object. The system 100 can then: scan the field of view of the optical sensor for the second object feature representing the second target object in Block S160; and, in response to detecting the second object feature in the field of view of the optical sensor, regularly calculate a second physical offset between the second target object and the end effector 140 in Block S110 based on a second position of the second object feature in the field of view of the optical sensor and the known offset between the optical sensor and the end effector 140. Once the end effector 140 has completed the first preplanned trajectory and grasped the first target object by the release position of the first preplanned trajectory, such as described above, the system 100 can drive the set of actuators to retract the end effector 140 from the release pose and then drive the set of actuators to reduce the second physical offset between the end effector 140 and the second object feature thereby moving the end effector 140 and the first target object toward the second target object in Block S180. Once the end effector 140 reaches a second interaction pose defined in a second interaction routine associated with the second target object, the system 100 can implement methods described above to execute the second interaction routine.

For example, the second interaction routine can be located relative to the second object feature and can define release of the first target object into the second target object (e.g., a basket); when the end effector 140 reaches the second interaction pose defined by the second interaction routine, the system 100 can lower the end effector 140 along a second preplanned trajectory toward a second release position just above the second target object, trigger the end effector 140 to release the first target object, and then retract the end effector 140 away from the second target object. The system 100 can then repeat the first and second interaction routines to engage a third target object and to move the third target object into or onto the second target object, etc.

However, the system 100 can automatically detect multiple target objects in the field of view of the optical sensor during an operating period in Block S160, such as based on virtual models of these target objects accessed in Block S310, and then string together multiple ad hoc trajectories and/or multiple preplanned trajectories between these target objects in any other way in Block S180.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for manipulating a multi-link robotic arm, the method comprising:
at a first time, recording a first optical image through an optical sensor arranged proximal a distal end of the robotic arm proximal an end effector;
detecting a global reference feature in a first position in the first optical image;
in response to detecting the global reference feature in the first optical image, virtually locating a preplanned trajectory relative to the first position of the global reference feature in the first optical image, the preplanned trajectory defining an object keypoint representing an estimated location of a target object within range of the end effector;
driving a set of actuators within the robotic arm to move the end effector along the preplanned trajectory, virtually located relative to the global reference feature, toward the object keypoint;
at a second time succeeding the first time, recording a second optical image through the optical sensor;
detecting an object feature in a second position in the second optical image, the object feature representing the target object;
in response to detecting the object feature in the second optical image, virtually aligning the object keypoint of the preplanned trajectory to the object feature based on the second position of the object feature in the second optical image; and
driving the set of actuators to move the end effector along the preplanned trajectory, virtually aligned to the object feature, toward the target object.

2. The method of claim 1:
further comprising, prior to the first time:
recording a sequence of keypoint images during manual manipulation of the end effector from a first pose to a second pose in real space during a setup routine; and
extracting positions of the global reference feature and positions of a template object feature from the sequence of keypoint images; and
compiling positions of the global reference feature and the object feature in the sequence of keypoint images into the preplanned trajectory comprising a first keypoint defining the first pose relative to the global reference feature and terminating at the object keypoint defining the second pose relative to the object feature;
wherein virtually locating the preplanned trajectory relative to the first position of the global reference feature in the first optical image comprises calculating a first offset between the first position of the global reference feature in the first optical image and a second keypoint position of the global reference feature in a first keypoint image in the preplanned trajectory;
wherein driving the set of actuators to move the end effector along the preplanned trajectory comprises driving the set of actuators to reduce the first offset;
wherein virtually aligning the object keypoint of the preplanned trajectory to the object feature comprises calculating a second offset between the second position of the object feature in the second optical image and a position of the template feature in a second keypoint image in the preplanned trajectory; and
wherein driving the set of actuators to move the end effector along the preplanned trajectory, virtually aligned to the object feature, comprises driving the set of actuators to reduce the second offset.

3. The method of claim 2:
wherein virtually locating the preplanned trajectory relative to the first position of the global reference feature in the first optical image comprises calculating a transform that maps the global reference feature in the first optical image to the global reference feature in the first keypoint image; and
wherein driving the set of actuators to reduce the first offset comprises driving the set of actuators as a function of the transform based on a stored motion model of the robotic arm.

4. The method of claim 1:
wherein virtually aligning the object keypoint of the preplanned trajectory to the object feature comprises:
calculating a position of the object feature relative to the robotic arm based on the second position, a skew, and a size of the object feature in the second optical image;
aligning the object keypoint of the preplanned trajectory to the position of the object feature;
redefining the preplanned trajectory from a keypoint in the preplanned trajectory adjacent the second pose of the end effector to the object keypoint aligned to the object feature; and
wherein driving the set of actuators to move the end effector along the preplanned trajectory, virtually aligned to the object feature, toward the target object comprises:
driving the set of actuators to move the end effector onto the preplanned trajectory virtually aligned to the object feature; and
in response to the end effector coinciding with the preplanned trajectory, driving the set of actuators to move the end effector along the preplanned trajectory toward the target object.

5. The method of claim 1:
wherein detecting the global reference feature in the first optical image comprises extracting the first position, a first skew, a first orientation, and a first size of the global reference feature from the first optical image;
wherein virtually locating the preplanned trajectory relative to the first position of the global reference feature in the first optical image comprises:
virtually locating an origin of a global reference frame based on the first position of the global reference feature;
aligning axes of the global reference frame within real space to the global reference feature based on the first skew, the first orientation, and the first size of the global reference feature in the first optical image; and
accessing the preplanned trajectory defined in the global reference frame;
wherein detecting the object feature in the second position in the second optical image comprises extracting the second position, a second skew, a second orientation, and a second size of the object feature from the second optical image;
wherein virtually aligning the object keypoint of the preplanned trajectory to the object feature comprises:
virtually locating an origin of an object reference frame based on the second position of the object feature;
aligning axes of the object reference frame within real space to the object reference feature based on the second skew, the second orientation, and the second size of the object reference feature in the second optical image; and
projecting the preplanned trajectory into the object reference frame with the object keypoint of the preplanned trajectory located relative to the object feature.

6. The method of claim 5:
wherein driving the set of actuators within the robotic arm to move the end effector along the preplanned trajectory, virtually located relative to the global reference feature, toward the object keypoint comprises:
calculating a first pose of the end effector within the global reference frame based on the first position, the first skew, the first orientation, and the first size of the global reference feature in the first optical image;
calculating a first offset between the first pose and the preplanned trajectory in the global reference frame; and
driving the set of actuators within the robotic arm to reduce the first offset; and
wherein driving the set of actuators to move the end effector along the preplanned trajectory, virtually aligned to the object feature, toward the target object comprises:
calculating a second pose of the end effector within the object reference frame based on the second position, the second skew, the second orientation, and the second size of the object reference feature in the second optical image;
calculating a second offset between the second pose and the preplanned trajectory in the object reference frame; and
driving the set of actuators within the robotic arm to reduce the second offset.

7. The method of claim 1:
wherein detecting the global reference feature in the first optical image comprises, at approximately the first time:
extracting a first constellation of features from the first optical image;
calculating a first confidence that the first constellation of features represents the global reference feature;
calculating a second confidence that the first constellation represents the object feature;
detecting presence of the global reference feature in a field of view of the optical sensor at approximately the first time in response to the first confidence exceeding a threshold value; and
detecting absence of the object feature in the field of view of the optical sensor at approximately the first time in response to the threshold value exceeding the second confidence;
wherein virtually locating the preplanned trajectory relative to the global reference feature comprises virtually aligning the preplanned trajectory relative to the global reference feature in response to detecting presence of the global reference feature and in response to detecting absence of the object feature in the field of view of the optical sensor;
wherein detecting the global reference feature in the first optical image comprises, at approximately the second time:
extracting a second constellation of features from the second optical image;
calculating a fourth confidence that the second constellation represents the object feature; and
detecting presence of the object feature in the field of view of the optical sensor at approximately the second time in response to the fourth confidence exceeding the threshold value; and wherein virtually aligning the object keypoint of the preplanned trajectory to the object feature comprises virtually aligning the object keypoint of the preplanned trajectory to the object feature in response to detecting presence of the object feature in the field of view of the optical sensor.

8. The method of claim 7:

further comprising:
- at an intermediate time succeeding the first time and preceding the second time, recording an intermediate optical image through the optical sensor;
- at approximately the intermediate time:
  - extracting an intermediate constellation of features from the intermediate image;
  - calculating a fifth confidence that the intermediate constellation of features represents the global reference feature;
  - calculating a sixth confidence that the intermediate constellation represents the object feature;
  - detecting presence of the global reference feature in the field of view of the optical sensor at approximately the intermediate time in response to the fifth confidence exceeding the threshold value; and
  - detecting presence of the object feature in the field of view of the optical sensor at approximately the intermediate time in response to the sixth confidence exceeding the threshold value; and
  - virtually locating the preplanned trajectory relative to the global reference feature in response to detecting presence of the global reference feature and in response to a resolution of the object feature in the field of view of the optical sensor remaining below a threshold resolution; and wherein virtually aligning the object keypoint of the preplanned trajectory to the object feature comprises virtually aligning the object keypoint of the preplanned trajectory to the object feature in response to detecting presence of the object feature in the field of view of the optical sensor and in response to a resolution of the object feature in the field of view of the optical sensor exceeding the threshold resolution.

9. The method of claim 7, further comprising:

in response to detecting presence of the global reference feature in the field of view of the optical sensor at approximately the first time, calculating a position of a global reference frame relative to the robotic arm at approximately the first time based on the first position of the global reference feature in the first optical image;

calculating a third confidence that the second constellation of features represents the global reference feature;

detecting presence of the global reference feature in the field of view of the optical sensor at approximately the second time in response to the third confidence exceeding the threshold value; and in response to detecting presence of the global reference feature in the field of view of the optical sensor at approximately the second time, recalculating the position of the global reference frame relative to the robotic arm at approximately the second time based on the second position of the global reference feature in the second optical image.

10. The method of claim 1, wherein detecting the global reference feature in the first position in the first optical image comprises detecting the global reference feature comprising a predefined reference fiducial arranged in a fixed position relative to a base of the robotic arm;

further comprising:
- accessing a virtual model of the target object;
- extracting a unique constellation of features from the virtual model; and
- associating the unique constellation of features with the target object; and wherein detecting the object feature in the second position in the second optical image comprises:
- extracting a set of features from the second optical image; and
- matching the set of features to the unique constellation of features to identify the target object in the second optical image.

11. The method of claim 10:

wherein detecting the global reference feature in the first position in the first optical image comprises detecting the predefined reference fiducial arranged on a fastener dispenser containing a set of threaded fasteners, the set of threaded fasteners comprising the target object; and wherein detecting the object feature in the second position in the second optical image comprises matching the set of features to the unique constellation of features representing a screw head to identify the target object in the second optical image.

12. The method of claim 1, further comprising:

at a third time succeeding the second time, driving the set of actuators to move the end effector into contact with the target object;

triggering the end effector to engage the target object;

virtually locating a second preplanned trajectory relative to the global reference feature, the second preplanned trajectory extending from the object keypoint to a target keypoint approximating a release position for the target object; and at a fourth time succeeding the third time, driving the set of actuators to move the end effector and the target object along the second preplanned trajectory away from the object keypoint and toward the target keypoint, the second preplanned trajectory virtually located relative to the global reference feature.

13. The method of claim 12:

further comprising:
- at approximately the fourth time, recording a fourth optical image through the optical sensor;
- detecting absence of the global reference feature and absence of a target feature in the fourth optical image, the target feature representing the release position for the target object;

wherein driving the set of actuators to move the end effector and the target object along the second preplanned trajectory comprises, at the fourth time, implementing closed-loop controls to retract the end effector along the second preplanned trajectory based on known lengths of segments of the robotic arm and outputs of angular position sensors arranged in joints between segments of the robotic arm in response to detecting absence of the global reference feature and absence of the target feature in the fourth optical image;

further comprising:
- at a fifth time succeeding the fourth time, recording a fifth optical image through the optical sensor;
- detecting the global reference feature in a fifth position in the fifth optical image;

in response to detecting the global reference feature in the fifth optical image, virtually locating the second preplanned trajectory relative to the fifth position of the global reference feature in the fifth optical image; and driving the set of actuators to move the end effector along the second preplanned trajectory, virtually located relative to the fifth position of the global reference feature in the fifth optical image, toward the target keypoint.

14. The method of claim 12:

further comprising:

at a sixth time succeeding the fourth time, recording a sixth optical image through the optical sensor;

detecting a target feature in a sixth position in the sixth optical image, the target feature representing the release position for the target object;

in response to detecting the target feature in the sixth optical image, virtually aligning the target keypoint of the second preplanned trajectory to the target feature based on the sixth position of the target feature in the sixth optical image; and driving the set of actuators to move the end effector along the second preplanned trajectory, virtually aligned to the target feature, toward the release position.

15. The method of claim 14, further comprising:

at a seventh time succeeding the sixth time, driving the set of actuators to move the end effector into the release position to contact the target object against a surface, the target object comprising a threaded fastener, and the release position coinciding with a bore;

in response to the target object entering the release position:

rotating the end effector; and driving the set of actuators to advance the end effector forward in a direction parallel to an axis of the target object and at a rate proportional to a rotational speed of the end effector; and in response to a torque on the end effector exceeding a threshold torque, driving the set of actuators to retract the end effector from the release position parallel to the axis of the target object.

16. The method of claim 12:

further comprising:

at an intermediate time succeeding the second time and preceding the third time, recording an intermediate optical image through the optical sensor;

detecting the object feature in an intermediate position in the intermediate optical image;

in response to detecting the intermediate object feature in the intermediate optical image:

characterizing a change in pose of the end effector in real space from the second time to the intermediate time based on a difference between the second position of the object feature in the second optical image and the intermediate position of the object feature in the intermediate image;

characterizing a sequence of outputs of angular position sensors in joints of the robotic arm from the second time to the intermediate time;

calibrating a motion model for the robotic arm based on the change in pose of the end effector in real space and the sequence of outputs of angular position sensors;

wherein driving the set of actuators to move the end effector into contact with the target object comprises:

at approximately the third time, recording a third optical image through the optical sensor;

detecting absence of the global reference feature and absence of the object feature in the third optical image;

in response to detecting absence of the global reference feature and absence of the object feature in the third optical image, driving the set of actuators to move the end effector into contact with the target object based on the motion model and outputs of the angular position sensors.

17. A method for manipulating a multi-link robotic arm, the method comprising:

at a first time, recording a first optical image through an optical sensor arranged proximal a distal end of the robotic arm proximal an end effector;

detecting a global reference feature in a first position in the first optical image;

virtually locating a global reference frame based on the first position of the global reference feature in the first optical image;

calculating a first pose of the end effector within the global reference frame at approximately the first time based on the first position of the global reference feature in the first optical image;

driving a set of actuators within the robotic arm to move the end effector from the first pose toward an object keypoint, the object keypoint defined within the global reference frame and representing an estimated location of a target object within range of the end effector;

at a second time succeeding the first time, recording a second optical image through the optical sensor;

detecting an object feature in a second position in the second optical image, the object feature representing the target object;

calculating a second pose of the end effector relative to the target object at approximately the first time based on the second position of the object feature in the second optical image; and driving the set of actuators to move the end effector from the second pose toward the target object.

18. The method of claim 17:

wherein virtually locating the global reference frame comprises virtually locating a preplanned trajectory based on the first position of the global reference feature in the first optical image, the preplanned trajectory defining a three-dimensional target path for the end effector within the global reference frame and terminating at the object keypoint defined within the global reference frame; and wherein driving the set of actuators to move the end effector from the first pose toward the object keypoint comprises driving the set of actuators to move the end effector from the first pose onto the preplanned trajectory and along the preplanned trajectory toward the object keypoint in the global reference frame;

further comprising, in response to detecting the object feature in the second optical image:

virtually locating an object reference frame based on the second position of the object feature in the second optical image; and projecting the preplanned trajectory into the object reference frame with the object keypoint aligned to the object based on the second position of the object feature in the second optical image; and wherein driving the set of actuators to move the end effector from the second pose toward the target object comprises driving the set of actuators to move the end effector from the second pose onto the preplanned trajectory and along the preplanned trajectory toward the object keypoint in the object reference frame.

19. A system comprising:
a base;
a robotic arm comprising:
   a first beam;
   a first joint interposed between first beam and base;
   a second beam; and
   a second joint interposed between the second beam and the first beam;
an end effector transiently coupled to the second beam opposite the second joint and defining an interface surface configured to engage a target object in the vicinity of the base;
an optical sensor coupled to the second beam, defining a field of view extending toward the end effector, and configured to output optical images of the field of view; and
a controller configured to:
   actuate the first joint and the second joint to move the end effector from an initial pose to a first pose according to a preplanned trajectory;
   identify the target object in a first optical image recorded by the optical sensor when the robotic arm occupies the first pose at a first time;
   align the preplanned trajectory to the target object based on a first position of the target object detected in the first optical image;
   actuate the first joint and the second joint to move the end effector from the first pose to a second pose along the preplanned trajectory aligned to the target object;
   identify the target object in a second optical image recorded by the optical sensor when the robotic arm occupies the second pose at a second time succeeding the first time;
   realign the preplanned trajectory to the target object based on a second position of the target object detected in the second optical image; and
   actuate the first joint and the second joint to move the end effector from the second pose to a third pose along the preplanned trajectory aligned to the target object.

20. The system of claim 19:
further comprising:
   a first angular position sensor arranged in the first joint; and
   a second angular position sensor arranged in the second joint;
wherein the controller is further configured to:
   calibrate motion of the first joint relative to outputs of the first angular position sensor and motion of the second joint relative to outputs of the second angular position sensor based on outputs of the first angular position sensor and the second angular position sensor from the first time to the second time and a difference between the first pose and the second pose;
   detect absence of the target object in a third optical image recorded by the optical sensor when the robotic arm occupies the third pose at a third time succeeding the second time; and
actuate the first joint and the second joint to move the end effector from the third pose to a fourth pose along the preplanned trajectory according to outputs of the first angular position sensor and the second angular position sensor.

* * * * *